(12) United States Patent
Couto et al.

(10) Patent No.: US 10,852,304 B2
(45) Date of Patent: Dec. 1, 2020

(54) MATERIALS AND METHODS FOR PERFORMING HISTOCHEMICAL ASSAYS FOR HUMAN PRO-EPIREGULIN AND AMPHIREGULIN

(71) Applicant: Ventana Medical Systems, Inc., Tucson, AZ (US)

(72) Inventors: Fernando Jose Rebelo do Couto, Pleasanton, CA (US); Zhiming Liao, Livermore, CA (US); Andrea Muranyi, Tucson, AZ (US); Kandavel Shanmugam, Chandler, AZ (US); Shalini Singh, Tucson, AZ (US); Yifei Zhu, San Jose, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 369 days.

(21) Appl. No.: 15/851,502

(22) Filed: Dec. 21, 2017

(65) Prior Publication Data

US 2018/0196057 A1 Jul. 12, 2018

Related U.S. Application Data

(63) Continuation of application No. PCT/EP2016/064883, filed on Jun. 27, 2016.

(60) Provisional application No. 62/186,251, filed on Jun. 29, 2015.

(51) Int. Cl.
| | | |
|---|---|---|
| C07K 16/00 | (2006.01) | |
| G01N 33/574 | (2006.01) | |
| C07K 16/22 | (2006.01) | |
| C07K 16/30 | (2006.01) | |

(52) U.S. Cl.
CPC ....... *G01N 33/57496* (2013.01); *C07K 16/22* (2013.01); *C07K 16/30* (2013.01); *C07K 2317/20* (2013.01); *C07K 2317/34* (2013.01); *C07K 2317/92* (2013.01); *G01N 2333/485* (2013.01)

(58) Field of Classification Search
None
See application file for complete search history.

(56) References Cited

FOREIGN PATENT DOCUMENTS

WO 2008044068 A2 4/2008

OTHER PUBLICATIONS

Jerkins et al., Beyond KRAS status and response to anti-EGFR therapy in metastatic colorectal cancer, Pharmacogenomics, 2014, pp. 1043-1052, 15 (7).
Ahlborg, N. et al, Generation of antibodies to human IL-12 and amphiregulin by immunization of Balb/c mice with diepitope multiple antigen peptides, Journal of Immunological Methods, (1997), pp. 23-32, vol. 204, Issue 1.
Cell Signaling Technology, EREG (D4051) Rabbit mAb, Cell Signaling Technology, (2014).
Eckstein, N. et al, Epidermal Growth Factor Receptor Pathway Analysis Identifies Amphiregulin as a Key Factor for Cisplatin Resistance of Human Breast Cancer Cells, Journal of Biological Chemistry, (2008), pp. 739-750, vol. 283, No. 2.
Fusanori Yotsumoto, et al, Amphiregulin regulates the activation of ERK and AKT through epidermal growth factor receptor and HER3 signals involved in the progression of pancreatic cancer, Cancer Science, (2010), pp. 2351-2360, vol. 101, issue 11.
Isokane, M. et al, Plasma-membrane-anchored growth factor pro-amphiregulin binds A-type lamin and regulates global transcription, Journal of Cell Science, (2008), pp. 3608-3618, vol. 121, issue 21.
Jonker, D.J., et al, Epiregulin gene expression as a biomarker of benefit from cetuximab in the treatment of advanced colorectal cancer, British Journal of Cancer, (2014), No. 3, pp. 648-655, vol. 110.
Pradhan, S.A., et al., Evidence that TSC2 acts as a transcription factor and bind to and represses the promoter of Epiregulin, Nucleic Acids Research, (2014), No. 10, pp. 6243-6255, vol. 42.
Zhang, J. et al., Intratumoral Epiregulin Is a Marker of Advanced Disease in Non-Small Cell Lung Cancer Patients and Confers Invasive Properties on EGFR-Mutant Cells, Cancer Prev Res, (2008), pp. 201-207, vol. 1.

*Primary Examiner* — Mark Halvorson
(74) *Attorney, Agent, or Firm* — Ventana Medical Systems, Inc.

(57) ABSTRACT

The invention provides anti-human pro-epiregulin and anti-human amphiregulin antibodies and methods of using the same. Anti-EREG antibodies raised against amino acids 148-169 and 156-169 of the human EREG protein, and anti-AREG antibodies raised against amino acids 238-252 of the human AREG protein are disclosed. Methods of using these antibodies to detect EREG and AREG and kits and other products for performing such methods are also disclosed.

19 Claims, 12 Drawing Sheets
(9 of 12 Drawing Sheet(s) Filed in Color)

Specification includes a Sequence Listing.

|  | J13H2L6 | J111H1L10 |
|---|---|---|
| AREG Negative |  |  |
| AREG Positive |  |  |

EREG

AREG

Membrane staining   Granular/punctate

MATERIALS AND METHODS FOR PERFORMING HISTOCHEMICAL ASSAYS FOR HUMAN PRO-EPIREGULIN AND AMPHIREGULIN

CROSS-REFERENCE TO RELATED APPLICATIONS

This is a continuation of PCT/EP2016/064883, filed Jun. 27, 2016, which claims the benefit of U.S. Provisional Patent Application No. 62/186,251, filed Jun. 29, 2015, the content of each of which is incorporated by reference herein in its entirety.

FIELD OF THE INVENTION

The present invention relates to antibodies for detecting epiregulin and amphiregulin in human samples and methods of using the same.

BACKGROUND

About 20% of patients with colon cancer present with metastatic colorectal cancer (mCRC) but regardless of the treatment they receive more than half (50-60%) of these patients will eventually develop incurable advanced disease, which has a 5 year survival rate of approximately 12.5%. Two signaling pathways in mCRC have been the focus of therapeutic drug development: the vascular endothelial growth factor receptor (VEGFR) and the epidermal growth factor receptor (EGFR) pathways. Currently, the majority of the patients with mCRC receive cytotoxic chemotherapy combined with either EGFR or VEGF-targeted therapies. EGFR is overexpressed in about 70% of CRC cases where it is associated with poor outcome. Targeted inhibition of EGFR with monoclonal antibodies, cetuximab or panitumumab, was approved by FDA in 2004 and 2006 to treat patients with mCRC. These antibodies target the extracellular domain of EGFR and compete with endogenous ligands to prevent activation of the receptor. By inhibiting EGFR signaling pathway these biological agents inhibit cell proliferation, differentiation, migration and metastasis. Both drugs have very similar efficacy with a 10-15% response rate.

Several molecular markers have been investigated to better predict response to anti-EGFR therapy. See Perkins et al., Pharmacogenetics, Vol. 15, Issue 7, pp. 1043-52 (2014). Clinical studies have provided evidence that EGFR inhibitors are the most effective in patients lacking RAS pathway mutations and maybe detrimental to those who have mutant type tumor. Point mutations in members of the RAS signaling pathways such as KRAS, NRAS, or BRAF lead to continuous activation downstream RAS-MAPK signaling, regardless of whether the EGFR is pharmacologically inactivated. In addition to RAS and BRAF mutations, other alternative mechanisms such as cMET or EGFR amplification play a role in resistance to Cetuximab or Panitumumab. PI3K-AKT-PTEN pathway can also be triggered by EGFR activation therefore mutation in PI3K or PTEN loss (often occur with KRAS or BRAF mutations) is also associated with a lack of response. RAS, BRAF, and PI3K mutations account for more than 60% of patients with mCRC that show de novo resistance to EGFR-targeted monoclonal antibodies. Of the 40% of patients with KRAS, NRAS, BRAF and PI3K wild type tumors (quadruple wild type patients), approximately half of these patients (only 15%) have a major benefit from anti-EGFR therapy and more than 20% are non-responders. Since RAS, RAF, PI3K status is not sufficient to evaluate anti-EGFR response; there is an unmet medical need to improve patients' selection for anti-EGFR therapy.

Several potential candidates are under investigations that are involved either in EGFR signaling pathway or in other pathways as MET or HER receptors. Elevated gene expression of epiregulin (EREG) and/or amphiregulin (AREG), ligands for EGFR has been consistently proposed for prediction of anti-EGFR therapy. In these tumors, anti-EGFR antibodies are competing with ligand-dependent activation of EGFR, leading to down regulation of the receptor from the cell surface, thus suppressing proliferative signaling. One recently published study showed that patients whose tumors had low EREG mRNA levels had no benefit from anti-EGFR therapy; the cetuximab therapy was not associated with an improvement in overall survival (OS). While in the biomarker positive group (KRAS wt/EREG high mRNA) the increased EREG mRNA expression was strongly associated with increased therapeutic benefit from cetuximab. In terms of absolute median OS gain, the addition of anti-EGFR therapy increased survival from 5.1 to 9.8 months compared to the best supportive care alone. This result suggests that EGFR ligands expression might become a clinically useful biomarker to screen patients with mCRC for EGFR inhibitor therapy.

It therefore would be useful to have new antibodies available for detection of EGFR ligands, such as EREG and AREG, in tissue samples.

SUMMARY

The present disclosure relates to anti-pro-epiregulin antibodies, anti-amphiregulin antibodies, and methods of using the same.

In one aspect, an antibody, antigen-binding fragment thereof, or a recombinant protein thereof is disclosed, wherein the antibody is capable of specifically binding to human pro-epiregulin, such as a human pro-epiregulin molecule according to SEQ ID NO: 1.

In one aspect, an antibody, antigen-binding fragment thereof, or a recombinant protein thereof is disclosed, wherein the antibody is capable of specifically binding to amino acids 148-169 of SEQ ID NO: 1.

In one aspect, an antibody, antigen-binding fragment thereof, or a recombinant protein thereof is disclosed, wherein the antibody is capable of specifically binding to human pro-epiregulin, wherein the antibody binds to an epitope comprising amino acid residues 148-169 of human pro-epiregulin polypeptide according to SEQ ID NO: 1. In some embodiments, the antibody comprises the following hypervariable regions (HVRs): (a) an HVR-H1 comprising the amino acid sequence of RYGMS (SEQ ID NO: 2); (b) an HVR-H2 comprising the amino acid sequence of SINRTAYTYYATWAKG (SEQ ID NO: 3); and (c) an HVR-H3 comprising the amino acid sequence of GLTYGGSDYDYDDAL (SEQ ID NO: 4). In some embodiments, the antibody further comprises the following heavy chain variable domain framework regions (FRs): (a) FR-H1 comprising the amino acid sequence of QSVEESGGRLVTPGTPLTLTCTVSGFSLS (SEQ ID NO: 5); (b) FR-H2 comprising the amino acid sequence of WVRQAPGKGLEYIG (SEQ ID NO: 6); (c) FR-H3 comprising the amino acid sequence of RFTISRTSTTVDLRMTSLTTEDTATYFCAR (SEQ ID NO: 7); and (d) FR-H4 comprising the amino acid sequence of WGPGTLVTVSS (SEQ ID NO: 8). In some embodiments, the antibody further comprises the following HVRs: (a) an HVR-L1 comprising the amino acid sequence of QASQSVYKNKNLA (SEQ ID NO: 9); (b) an HVR-L2 comprising the amino acid sequence of RASTLAS (SEQ ID NO: 10); and (c) an HVR-L3 comprising the amino acid sequence of QGEFSCSTFDCIL (SEQ ID NO: 11). In some embodiments, the antibody further comprises the following light chain variable domain FRs: (a) FR-L1 comprising the amino acid sequence of QVLTQTPSSVSAAVG-GTVTINC (SEQ ID NO: 12); (b) FR-L2 comprising the amino acid sequence of WYQQKPGQPPKLLIY (SEQ ID NO: 13); (c) FR-L3 comprising the amino acid sequence of GVSSRFKGSGSGTQFTLTISGVQCADAATYYC (SEQ ID NO: 14); and (d) FR-L4 comprising the amino acid sequence of FGGGTEMVVK (SEQ ID NO: 15). In some embodiments, the antibody comprises (a) a VH sequence having at least 95% sequence identity to the amino acid sequence of SEQ ID NO: 16; (b) a VL sequence having at least 95% sequence identity to the amino acid sequence of SEQ ID NO: 17; or (c) a VH sequence as in (a) and a VL sequence as in (b). In some embodiments, the antibody comprises a VH sequence of SEQ ID NO: 16. In some embodiments, the antibody comprises a VL sequence of SEQ ID NO: 17.

In other embodiments, the antibody comprises the following HVRs: (a) an HVR-L1 comprising the amino acid sequence of QASQSVYKNKNLA (SEQ ID NO: 9); (b) an HVR-L2 comprising the amino acid sequence of RASTLAS (SEQ ID NO: 10); and (c) an HVR-L3 comprising the amino acid sequence of QGEFSCSTFDCIL (SEQ ID NO: 11). In some embodiments, the antibody further comprises the following light chain variable domain FRs: (a) FR-L1 comprising the amino acid sequence of QVLTQTPSSVSAAVG-GTVTINC (SEQ ID NO: 12); (b) FR-L2 comprising the amino acid sequence of WYQQKPGQPPKLLIY (SEQ ID NO: 13); (c) FR-L3 comprising the amino acid sequence of GVSSRFKGSGSGTQFTLTISGVQCADAATYYC (SEQ ID NO: 14); and (d) FR-L4 comprising the amino acid sequence of FGGGTEMVVK (SEQ ID NO: 15).

In another aspect, the invention features an isolated antibody that specifically binds human pro-epiregulin, wherein the antibody comprises the following HVRs: (a) an HVR-H1 comprising the amino acid sequence of RYGMS (SEQ ID NO: 2); (b) an HVR-H2 comprising the amino acid sequence of SINRTAYTYYATWAKG (SEQ ID NO: 3); (c) an HVR-H3 comprising the amino acid sequence of GLTYGGSDY-DYDDAL (SEQ ID NO: 4); (d) an HVR-L1 comprising the amino acid sequence of QASQSVYKNKNLA (SEQ ID NO: 9); (e) an HVR-L2 comprising the amino acid sequence of RASTLAS (SEQ ID NO: 10); and (f) an HVR-L3 comprising the amino acid sequence of QGEFSCSTFDCIL (SEQ ID NO: 11). In some embodiments, the antibody further comprises the following heavy chain variable domain and light chain variable domain FRs: (a) FR-H1 comprising the amino acid sequence of QSVEESGGRLVTPGTPLTLTCTVSGF-SLS (SEQ ID NO: 5); (b) FR-H2 comprising the amino acid sequence of WVRQAPGKGLEYIG (SEQ ID NO: 6); (c) FR-H3 comprising the amino acid sequence of RFTISRT-STTVDLRMTSLTTEDTATYFCAR (SEQ ID NO: 7); (d) FR-H4 comprising the amino acid sequence of WGPGTLVTVSS (SEQ ID NO: 8); (e) FR-L1 comprising the amino acid sequence of QVLTQTPSSVSAAVGGT-VTINC (SEQ ID NO: 12); (f) FR-L2 comprising the amino acid sequence of WYQQKPGQPPKLLIY (SEQ ID NO: 13); (g) FR-L3 comprising the amino acid sequence of GVSSRFKGSGSGTQFTLTISGVQCADAATYYC (SEQ ID NO: 14); and (h) FR-L4 comprising the amino acid sequence of FGGGTEMVVK (SEQ ID NO: 15). In some embodiments, the antibody comprises a VH sequence of SEQ ID NO: 16 and a VL sequence of SEQ ID NO: 17.

In one aspect, an antibody, antigen-binding fragment thereof, or a recombinant protein thereof is disclosed, wherein the antibody is capable of specifically binding to amino acids 156-169 of SEQ ID NO: 1.

In one aspect, an antibody, antigen-binding fragment thereof, or a recombinant protein thereof is disclosed, wherein the antibody is capable of specifically binding to human pro-epiregulin, wherein the antibody binds to an epitope comprising amino acid residues 156-169 of human pro-epiregulin polypeptide according to SEQ ID NO: 1. In some embodiments, the antibody comprises the following hypervariable regions (HVRs): (a) an HVR-H1 comprising the amino acid sequence of TFAMA (SEQ ID NO: 18); (b) an HVR-H2 comprising the amino acid sequence of FISLS-DATYYATWAKG (SEQ ID NO: 19); and (c) an HVR-H3 comprising the amino acid sequence of VVGDSSGYPNT-FHP (SEQ ID NO: 20). In some embodiments, the antibody further comprises the following heavy chain variable domain framework regions (FRs): (a) FR-H1 comprising the amino acid sequence of KSVEESGGRLVTPGTPLTLTCT-VSGIDLS (SEQ ID NO: 21); (b) FR-H2 comprising the amino acid sequence of WVRQAPGKGLEYIG (SEQ ID NO: 22); (c) FR-H3 comprising the amino acid sequence of RFTISKSSSTTVDLKIITPTAEDTATYFCAR (SEQ ID NO: 23); and (d) FR-H4 comprising the amino acid sequence of WGPGTLVTVSS (SEQ ID NO: 24). In some embodiments, the antibody further comprises the following HVRs: (a) an HVR-L1 comprising the amino acid sequence of QASQSIHNSDFLA (SEQ ID NO: 25) or QASQNIHNSDFLA (SEQ ID NO: 26); (b) an HVR-L2 comprising the amino acid sequence of RASKLPS (SEQ ID NO: 27); and (c) an HVR-L3 comprising the amino acid sequence of QGTYYSGGWYFT (SEQ ID NO: 28). In some embodiments, the antibody further comprises the following light chain variable domain FRs: (a) FR-L1 comprising the amino acid sequence of QVLTQTPSPVSAAVGGTVTINC (SEQ ID NO: 29); (b) FR-L2 comprising the amino acid sequence of WYQQKPGQPPKLLIY (SEQ ID NO: 30); (c) FR-L3 comprising the amino acid sequence of GVPSRFK-GSGSGTQFTLTISDLECDDAATYYC (SEQ ID NO: 31); and (d) FR-L4 comprising the amino acid sequence of FGGGTEVVVK (SEQ ID NO: 32). In some embodiments, the antibody comprises (a) a VH sequence having at least 95% sequence identity to the amino acid sequence of SEQ ID NO: 33; (b) a VL sequence having at least 95% sequence identity to the amino acid sequence of SEQ ID NO: 34 or SEQ ID NO: 35; or (c) a VH sequence as in (a) and a VL sequence as in (b). In some embodiments, the antibody comprises a VH sequence of SEQ ID NO: 33. In some embodiments, the antibody comprises a VL sequence of SEQ ID NO: 34 or SEQ ID NO: 35. In some embodiments, the antibody comprises a VH sequence of SEQ ID NO: 33 and a VL sequence of SEQ ID NO: 34. In some embodiments, the antibody comprises a VH sequence of SEQ ID NO: 33 and a VL sequence of SEQ ID NO: 35.

In other embodiments, the antibody comprises the following HVRs: (a) an HVR-L1 comprising the amino acid sequence of QASQSIHNSDFLA (SEQ ID NO: 25) OR QASQNIHNSDFLA (SEQ ID NO: 26); (b) an HVR-L2 comprising the amino acid sequence of RASKLPS (SEQ ID NO: 27); and (c) an HVR-L3 comprising the amino acid sequence of QGTYYSGGWYFT (SEQ ID NO: 28). In some embodiments, the antibody further comprises the following light chain variable domain FRs: (a) FR-L1 comprising the amino acid sequence of QVLTQTPSPVSAAVGGTVTINC (SEQ ID NO: 29); (b) FR-L2 comprising the amino acid sequence of WYQQKPGQPPKLLIY (SEQ ID NO: 30); (c) FR-L3 comprising the amino acid sequence of GVPSRFK-GSGSGTQFTLTISDLECDDAATYYC (SEQ ID NO: 31); and (d) FR-L4 comprising the amino acid sequence of FGGGTEVVVK (SEQ ID NO: 32).

In another aspect, the invention features an isolated antibody that specifically binds human pro-epiregulin, wherein the antibody comprises the following HVRs: (a) an HVR-H1 comprising the amino acid sequence of TFAMA (SEQ ID NO: 18); (b) an HVR-H2 comprising the amino acid sequence of FISLSDATYYATWAKG (SEQ ID NO: 19); (c) an HVR-H3 comprising the amino acid sequence of VVGDSSGYPNTFHP (SEQ ID NO: 20); (d) an HVR-L1 comprising the amino acid sequence of QASQSIHNSDFLA (SEQ ID NO: 25) OR QASQNIHNSDFLA (SEQ ID NO: 26); (e) an HVR-L2 comprising the amino acid sequence of RASKLPS (SEQ ID NO: 27); and (f) an HVR-L3 comprising the amino acid sequence of QGTYYSGGWYFT (SEQ ID NO: 28). In some embodiments, the antibody further comprises the following heavy chain variable domain and light chain variable domain FRs: (a) FR-H1 comprising the amino acid sequence of KSVEESGGRLVTPGTPLTLTCT-VSGIDLS (SEQ ID NO: 21); (b) FR-H2 comprising the amino acid sequence of WVRQAPGKGLEYIG (SEQ ID NO: 22); (c) FR-H3 comprising the amino acid sequence of RFTISKSSSTTVDLKIITPTAEDTATYFCAR (SEQ ID NO: 23); (d) FR-H4 comprising the amino acid sequence of WGPGTLVTVSS (SEQ ID NO: 24); (e) FR-L1 comprising the amino acid sequence of QVLTQTPSPVSAAVGGT-VTINC (SEQ ID NO: 29); (f) FR-L2 comprising the amino acid sequence of WYQQKPGQPPKLLIY (SEQ ID NO: 30); (g) FR-L3 comprising the amino acid sequence of GVPSRFKGSGSGTQFTLTISDLECDDAATYYC (SEQ ID NO: 31); and (h) FR-L4 comprising the amino acid sequence of FGGGTEVVVK (SEQ ID NO: 32). In some embodiments, the antibody comprises a VH sequence of SEQ ID NO: 33 and a VL sequence of SEQ ID NO: 34 or SEQ ID NO: 35.

In another aspect, the invention features an isolated antibody that competes for binding to human pro-epiregulin with any one of the preceding anti-pro-epiregulin antibodies.

In one aspect, an antibody, antigen-binding fragment thereof, or a recombinant protein thereof is disclosed, wherein the antibody is capable of specifically binding to amphiregulin.

In one aspect, an antibody, antigen-binding fragment thereof, or a recombinant protein thereof is disclosed, wherein the antibody is capable of specifically binding to amino acids 238-252 of SEQ ID NO: 36.

In one aspect, an antibody, antigen-binding fragment thereof, or a recombinant protein thereof is disclosed, wherein the antibody is capable of specifically binding to amphiregulin, wherein the antibody binds to an epitope comprising amino acid residues 238-252 of a human amphiregulin polypeptide (such as SEQ ID NO: 36). In some embodiments, the antibody comprises the following hypervariable regions (HVRs): (a) an HVR-H1 comprising the amino acid sequence of SYAIS (SEQ ID NO: 37); (b) an HVR-H2 comprising the amino acid sequence of FIVGSSGSAYYASWAKS (SEQ ID NO: 38); and (c) an HVR-H3 comprising the amino acid sequence of GLYSGGNY (SEQ ID NO: 39). In some embodiments, the antibody further comprises the following heavy chain variable domain framework regions (FRs): (a) FR-H1 comprising the amino acid sequence of QSLEESRGGLIKPG-GTLTLTCTVSGFSLS (SEQ ID NO: 40); (b) FR-H2 comprising the amino acid sequence of WVRQAPGN-GLEWIG (SEQ ID NO: 41); (c) FR-H3 comprising the amino acid sequence of RSTITRDTNLNTVTLKMT-SLTAADTATYFCAK (SEQ ID NO: 42); and (d) FR-H4 comprising the amino acid sequence of WGPGTLVTVSS (SEQ ID NO: 43). In some embodiments, the antibody further comprises the following HVRs: (a) an HVR-L1 comprising the amino acid sequence of QSSQSVDEN-NYLS (SEQ ID NO: 44); (b) an HVR-L2 comprising the amino acid sequence of RASTLES (SEQ ID NO: 45); and (c) an HVR-L3 comprising the amino acid sequence of LGGYSGYSDDG (SEQ ID NO: 46). In some embodiments, the antibody further comprises the following light chain variable domain FRs: (a) FR-L1 comprising the amino acid sequence of AVLTQTPSPVSAAVGGTVSISC (SEQ ID NO: 47); (b) FR-L2 comprising the amino acid sequence of WFQQKPGQPPKLLIY (SEQ ID NO: 48); (c) FR-L3 comprising the amino acid sequence of GVPSRFSGSGS-GTQFTLTVSGVQCDDAATYYC (SEQ ID NO: 49); and (d) FR-L4 comprising the amino acid sequence of FGGGTEVVVK (SEQ ID NO: 50). In some embodiments, the antibody comprises (a) a VH sequence having at least 95% sequence identity to the amino acid sequence of SEQ ID NO: 51; (b) a VL sequence having at least 95% sequence identity to the amino acid sequence of SEQ ID NO: 52; or (c) a VH sequence as in (a) and a VL sequence as in (b). In some embodiments, the antibody comprises a VH sequence of SEQ ID NO: 51. In some embodiments, the antibody comprises a VL sequence of SEQ ID NO: 52.

In other embodiments, the antibody comprises the following HVRs: (a) an HVR-L1 comprising the amino acid sequence of QSSQSVDENNYLS (SEQ ID NO: 44); (b) an HVR-L2 comprising the amino acid sequence of RASTLES (SEQ ID NO: 45); and (c) an HVR-L3 comprising the amino acid sequence of LGGYSGYSDDG (SEQ ID NO: 46). In some embodiments, the antibody further comprises the following light chain variable domain FRs: (a) FR-L1 comprising the amino acid sequence of AVLTQTPSPVSAAVG-GTVSISC (SEQ ID NO: 47); (b) FR-L2 comprising the amino acid sequence of WFQQKPGQPPKLLIY (SEQ ID NO: 48); (c) FR-L3 comprising the amino acid sequence of GVPSRFSGSGSGTQFTLTVSGVQCDDAATYYC (SEQ ID NO: 49); and (d) FR-L4 comprising the amino acid sequence of FGGGTEVVVK (SEQ ID NO: 50).

In another aspect, the invention features an isolated antibody that specifically binds amphiregulin, wherein the antibody comprises the following HVRs: (a) an HVR-H1 comprising the amino acid sequence of SYAIS (SEQ ID NO: 37); (b) an HVR-H2 comprising the amino acid sequence of FIVGSSGSAYYASWAKS (SEQ ID NO: 38); (c) an HVR-H3 comprising the amino acid sequence of GLYSGGNY (SEQ ID NO: 39); (d) an HVR-L1 comprising the amino acid sequence of QSSQSVDENNYLS (SEQ ID NO: 44); (e) an HVR-L2 comprising the amino acid sequence of RASTLES (SEQ ID NO: 45); and (f) an HVR-L3 comprising the amino acid sequence of LGGYSGYSDDG (SEQ ID NO: 46). In some embodiments, the antibody further comprises the following heavy chain variable domain and light chain variable domain FRs: (a) FR-H1 comprising the amino acid sequence of QSLEESRGGLIKPGGTLTLTCTVSGF-SLS (SEQ ID NO: 40); (b) FR-H2 comprising the amino acid sequence of WVRQAPGNGLEWIG (SEQ ID NO: 41); (c) FR-H3 comprising the amino acid sequence of RSTITRDTNLNTVTLKMTSLTAADTATYFCAK (SEQ ID NO: 42); (d) FR-H4 comprising the amino acid sequence of WGPGTLVTVSS (SEQ ID NO: 43); (e) FR-L1 comprising the amino acid sequence of AVLTQTPSPVSAAVGGT- VSISC (SEQ ID NO: 47); (f) FR-L2 comprising the amino acid sequence of WFQQKPGQPPKLLIY (SEQ ID NO: 48); (g) FR-L3 comprising the amino acid sequence of GVPSRF-SGSGSGTQFTLTVSGVQCDDAATYYC (SEQ ID NO: 49); and (h) FR-L4 comprising the amino acid sequence of FGGGTEVVVK (SEQ ID NO: 50). In some embodiments, the antibody comprises a VH sequence of SEQ ID NO: 51 and a VL sequence of SEQ ID NO: 52.

In another aspect, the invention features an isolated antibody that competes for binding to amphiregulin with any one of the preceding anti-amphiregulin antibodies.

In another aspect, the invention features an isolated antibody that binds to the same epitope as any one of the preceding antibodies.

In some embodiments, any one of the preceding antibodies can be a monoclonal antibody. In some embodiments, the monoclonal antibody can be a rabbit monoclonal antibody.

In some embodiments, any one of the preceding antibodies can be an antibody fragment that specifically binds human pro-epiregulin. In some embodiments, the antibody fragment is selected from the group consisting of Fab, single chain variable fragment (scFv), Fv, Fab', Fab'-SH, F(ab')2, and diabody.

In another aspect, the invention features an immunoconjugate comprising any one of the preceding antibodies.

In another aspect, the invention features an isolated nucleic acid that encodes any of the antibodies described herein. In another aspect, the invention features a vector (e.g., an expression vector) comprising the nucleic acid for expressing the antibody. In another aspect, the invention features host cells comprising the preceding nucleic acids and/or vectors.

In some aspects, any one of the preceding antibodies can be for use in detecting the presence or expression level of human pro-epiregulin and/or amphiregulin in a biological sample. In some embodiments, the detecting is by immunohistochemistry (IHC), immunofluorescence (IF), or immunoblot. In some embodiments, the detecting is by IHC. In some embodiments, the sample comprises a fixed tissue. In some embodiments, the fixed tissue is a formalin-fixed paraffin-embedded (FFPE) tissue. In some embodiments, the sample is from a subject having, or predisposed to, cancer or an autoimmune disease.

A further aspect of the invention is a method of detecting the presence or expression level of human pro-epiregulin and/or amphiregulin in a biological sample comprising contacting the biological sample with any one of the preceding antibodies and detecting the presence of the bound antibody. In some embodiments, the detecting is by IHC, IF, or immunoblot. In some embodiments, the detecting is by IHC. In some embodiments, the sample comprises a fixed tissue. In some embodiments, the fixed tissue is a FFPE tissue. In some embodiments, the sample is from a subject having or predisposed to cancer or autoimmune disease.

SEQUENCE LISTING INCORPORATION BY REFERENCE

This application hereby incorporates-by-reference a sequence listing submitted herewith in a computer-readable format, having a file name of 32945US1_ST25, created on 5 Dec. 20, 2017, which is 20,030 bytes in size.

BRIEF DESCRIPTION OF THE DRAWINGS

The application file contains at least one drawing executed in color. Copies of this patent or patent application with color drawings will be provided by the Office upon request and payment of the necessary fee.

DETAILED DESCRIPTION OF EMBODIMENTS OF THE INVENTION

I. Definitions

Figure 1:
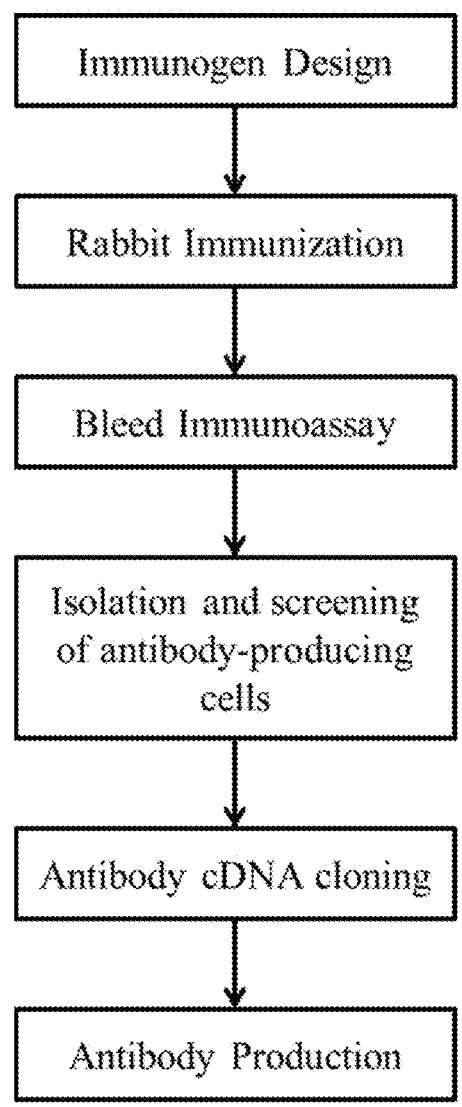
FIG. 1 is a schematic diagram showing the general antibody production process for the anti-human pro-epiregulin and anti-human amphiregulin antibodies.

The terms "anti-human pro-epiregulin antibody," "anti-human pro-epiregulin antibody," "antibody that specifically binds to human pro-epiregulin," and "antibody that binds to human pro-epiregulin" refer to an antibody that is capable of binding human pro-epiregulin with sufficient affinity such that the antibody is useful as a diagnostic and/or therapeutic agent in targeting human pro-epiregulin. In one embodiment, the extent of binding of an anti-human pro-epiregulin antibody to an unrelated, non-human pro-epiregulin protein is less than about 10% of the binding of the antibody to human pro-epiregulin as measured, e.g., by a radioimmunoassay (RIA). In certain embodiments, an antibody that binds to human pro-epiregulin has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-human pro-epiregulin antibody binds to an epitope of human pro-epiregulin that is conserved among human pro-epiregulin from different species.

The terms "anti-human amphiregulin antibody," "anti-human amphiregulin antibody," "antibody that specifically binds to human amphiregulin," and "antibody that binds to human amphiregulin" refer to an antibody that is capable of binding human amphiregulin with sufficient affinity such that the antibody is useful as a diagnostic and/or therapeutic agent in targeting human amphiregulin. In one embodiment, the extent of binding of an anti-human amphiregulin antibody to an unrelated, non-human amphiregulin protein is less than about 10% of the binding of the antibody to human amphiregulin as measured, e.g., by a radioimmunoassay (RIA). In certain embodiments, an antibody that binds to human amphiregulin has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-human amphiregulin antibody binds to an epitope of human amphiregulin that is conserved among human amphiregulin from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

An "autoimmune disease" is a disease or disorder arising from and directed against an individual's own tissues or organs or a co-segregation or manifestation thereof or resulting condition therefrom. Autoimmune diseases can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Non-limiting exemplary autoimmune diseases include autoimmune rheumatologic disorders (such as, for example, RA, Sjogren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases {e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjogren's syndrome, Graves' disease, IDDM, pernicious anemia, thyroiditis, and glomerulonephritis.

By "biological sample" is meant a collection of similar cells obtained from a subject or patient. A biological sample can be a tissue or a cell sample. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The biological sample can also be obtained from in vitro tissue or cell culture. The tissue sample may contain compounds which are not naturally intermixed with the tissue in nature such as preservatives, anticoagulants, buffers, fixatives, nutrients, antibiotics, or the like. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer. In one specific embodiment, the biological sample is a sample of a colorectal tumor. In another specific embodiment, the biological sample is a sample of a breast tumor. In another specific embodiment, the biological sample is a sample of a lung tumor, such as non-small cell lung carcinoma.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest.* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

The terms "level of expression" or "expression level" in general are used interchangeably and generally refer to the amount of a polynucleotide, mRNA, or an amino acid product or protein in a biological sample. "Expression" generally refers to the process by which gene-encoded information is converted into the structures present and operating in the cell. Therefore, according to the invention "expression" of a gene (e.g., the human pro-epiregulin gene) may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. In some embodiments, "expression level" refers to amount of a protein (e.g., human pro-epiregulin) in a biological sample as determined using immunohistochemistry immunoblotting (e.g., Western blotting), immunofluorescence (IF), Enzyme-Linked Immunosorbant Assay (ELISA), or flow cytometry.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest.* Fifth Edition, NIH Publication 91-3242, Bethesda Md., Vols. 1-3, 1991. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia et al. *J. Mol. Biol.* 196: 901-917, 1987);

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest.* 5th Ed. Public Health Service, National Institutes of Health, Bethesda, Md., 1991);

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745, 1996); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3). Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al. *J. Chromatogr. B.* 848: 79-87, 2007.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human pro-epiregulin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Isolated nucleic acid encoding an anti-human amphiregulin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pro-epiregulin," as used herein, refers to any native pro-epiregulin from any vertebrate source, including mammals such as primates (e.g., humans) and rodents (e.g., mice and rats), unless otherwise indicated, but does not include the cleaved and secreted form, which is referred to as "epiregulin". The term encompasses "full-length," unprocessed human pro-epiregulin as well as any form of human pro-epiregulin that results from processing in the cell, except for the cleaved and secreted form of epiregulin. The term also encompasses naturally occurring variants of human pro-epiregulin, e.g., splice variants or allelic variants. The canonical pro-epiregulin molecule is a 169 amino acid single pass type-I membrane protein that is cleaved to a secreted molecule (termed epiregulin) containing amino acids amino acids 60-108 and which acts as a ligand of EGFR. See Uniprot Entry 014944. Additional information on the human pro-epiregulin gene, including the genomic DNA sequence, can be found under NCBI Gene ID No. 2069. The amino acid sequence of an exemplary full-length human pro-epiregulin protein can be found, e.g., under NCBI Accession No. BAA22146 or UniProt Accession No. 014944, and herein at SEQ ID NO: 36.

The term "amphiregulin," as used herein, refers to any native amphiregulin from any vertebrate source, including mammals such as primates (e.g., humans) and rodents (e.g., mice and rats), unless otherwise indicated, but does not include the cleaved and secreted form. The term encompasses "full-length," unprocessed human amphiregulin as well as any form of human amphiregulin that results from processing in the cell, except for the cleaved and secreted form. The term also encompasses naturally occurring variants of human amphiregulin, e.g., splice variants or allelic variants. The canonical amphiregulin molecule is a 252 amino acid single pass type-I membrane protein that is cleaved at Lysine 187 to form a secreted EGFR ligand. See Uniprot Entry P15514; Levano and Kenny, FEBS Letters, Vol. 586, Issue 19, pp. 3500-02 (2012). Additional information on the human amphiregulin gene, including the genomic DNA sequence, can be found under NCBI Gene ID No. 374. The amino acid sequence of an exemplary full-length human pro-epiregulin protein can be found, e.g., under NCBI Accession No. NP 001648 or UniProt Accession No. P15514, and herein at SEQ ID NO: 36.

As used herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope, e.g., amino acid residues 148-169 of a human pro-epiregulin according to SEQ ID NO: 1 or amino acid residues 238-252 of a human amphiregulin according to SEQ ID NO: 36) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

A "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al. *Kuby Immunology.* 6$^{th}$ ed., page 91, W.H. Freeman and Co., 2007. A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al. *J. Immunol.* 150: 880-887, 1993 and Clarkson et al. *Nature.* 352: 624-628, 1991.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

The invention provides novel antibodies that bind to human pro-epiregulin. Antibodies of the invention are useful, for example, for detecting the presence of human pro-epiregulin or the expression level of human pro-epiregulin (e.g., in biological samples).

The invention also provides novel antibodies that bind to human amphiregulin. Antibodies of the invention are useful, for example, for detecting the presence of human amphiregulin or the expression level of human amphiregulin (e.g., in biological samples).

A. Exemplary Anti-Human Pro-Epiregulin Antibodies

The invention provides anti-human pro-epiregulin antibodies useful for, e.g., diagnostic applications (e.g., immunohistochemistry immunofluorescence (IF), and immunoblot (e.g., Western blot)). In one example, the invention provides anti-human pro-epiregulin antibodies that bind to an epitope including amino acid residues 148-169 of human pro-epiregulin (e.g., amino acid residues 148-169 of SEQ ID NO: 1), which is located at the carboxy terminus of the pro-epiregulin molecule. In one example, the invention provides anti-human pro-epiregulin antibodies that bind to an epitope including amino acid residues 156-169 of human pro-epiregulin (e.g., amino acid residues 156-169 of SEQ ID NO: 1), which is located at the carboxy terminus of the pro-epiregulin molecule. The epitope on human pro-epiregulin may be recognized in a manner that is conformation-dependent or conformation-independent.

In some instances, the anti-human pro-epiregulin antibodies that bind to amino acid residues 148-169 of human proepiregulin include at least one, two, three, four, five, or six HVRs selected from (a) HVR-H1 comprising SEQ ID NO: 2; (b) HVR-H2 comprising SEQ ID NO: 3; (c) HVR-H3 comprising SEQ ID NO: 4; (d) HVR-L1 comprising SEQ ID NO: 9; (e) HVR-L2 comprising SEQ ID NO: 10; and (f) HVR-L3 comprising SEQ ID NO: 11. For example, in some instances, the anti-human pro-epiregulin antibodies include (a) an HVR-H1 comprising SEQ ID NO: 2; (b) an HVR-H2 comprising SEQ ID NO: 3; and (c) an HVR-H3 comprising SEQ ID NO: 4. In some instances, the anti-human pro-epiregulin antibodies include (a) an HVR-L1 comprising SEQ ID NO: 9; (b) HVR-L2 comprising SEQ ID NO: 10; and (c) HVR-L3 comprising SEQ ID NO: 11.

In some instances wherein the anti-human pro-epiregulin antibodies bind to amino acid residues 148-169 of human pro-epiregulin and include (a) an HVR-H1 comprising SEQ ID NO: 2; (b) an HVR-H2 comprising SEQ ID NO: 3; and (c) an HVR-H3 comprising SEQ ID NO: 4, the anti-human pro-epiregulin antibodies further include the following heavy chain variable domain framework regions (FRs): (a) FR-H1 comprising SEQ ID NO: 5; (b) FR-H2 comprising SEQ ID NO: 6; (c) FR-H3 comprising SEQ ID NO: 7; or (d) FR-H4 comprising SEQ ID NO: 8. In some instances wherein the anti-human pro-epiregulin antibodies bind to amino acid residues 148-169 of human pro-epiregulin and include (a) an HVR-H1 comprising SEQ ID NO: 2; (b) an HVR-H2 comprising SEQ ID NO: 3; and (c) an HVR-H3 comprising SEQ ID NO: 4, the anti-human pro-epiregulin antibodies further include the following heavy chain variable domain framework regions (FRs): (a) FR-H1 comprising SEQ ID NO: 5; (b) FR-H2 comprising SEQ ID NO: 6; (c) FR-H3 comprising SEQ ID NO: 7; and (d) FR-H4 comprising SEQ ID NO: 8.

In some instances wherein the anti-human pro-epiregulin antibodies bind to amino acid residues 148-169 of human proepiregulin, the antibodies include (a) an HVR-H1 comprising SEQ ID NO: 2; (b) an HVR-H2 comprising SEQ ID NO: 3; (c) an HVR-H3 comprising SEQ ID NO: 4; (d) an HVR-L1 comprising SEQ ID NO: 9; (e) an HVR-L2 comprising SEQ ID NO: 10; and (f) an HVR-L3 comprising SEQ ID NO: 11. In some instances, these anti-human pro-epiregulin antibodies include the following FRs: (a) FR-H1 comprising SEQ ID NO: 5; (b) FR-H2 comprising SEQ ID NO: 6; (c) FR-H3 comprising SEQ ID NO: 7; and (d) FR-H4 comprising SEQ ID NO: 8 and may additionally or alternatively include (e) FR-L1 comprising SEQ ID NO: 12; (f) FR-L2 comprising SEQ ID NO: 13; (g) FR-L3 comprising SEQ ID NO: 14; and (h) FR-L4 comprising SEQ ID NO: 15.

In some instances, the anti-human pro-epiregulin antibodies that bind to amino acid residues 148-169 of human pro-epiregulin may also include a heavy chain variable domain (VH) sequence having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 16. In certain embodiments, a VH sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 16), but an anti-human pro-epiregulin antibody including that sequence retains the ability to bind to human pro-epiregulin. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 16. In certain embodiments, substitutions, insertions, or deletions occur in regions outside the HVRs (i.e., in the FRs). Optionally, the anti-human pro-epiregulin antibodies include the VH sequence in SEQ ID NO: 16, including post-translational modifications of that sequence. In a particular embodiment, the VH comprises one, two, or three HVRs selected from: (a) HVR-H1 comprising SEQ ID NO: 2, (b) HVR-H2 comprising SEQ ID NO: 3, and (c) HVR-H3 comprising SEQ ID NO: 4.

In some instances, the anti-human pro-epiregulin antibodies that bind to amino acid residues 148-169 of human pro-epiregulin may also include a light chain variable domain (VL) having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 17. In certain embodiments, a VL sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 17), but an anti-human pro-epiregulin antibody including that sequence retains the ability to bind to human pro-epiregulin. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 17. In certain embodiments, the substitutions, insertions, or deletions occur in regions outside the HVRs (i.e., in the FRs). Optionally, the anti-human pro-epiregulin antibody comprises the VL sequence in SEQ ID NO: 17, including post-translational modifications of that sequence. In a particular embodiment, the VL comprises one, two or three HVRs selected from (a) HVR-L1 comprising SEQ ID NO: 9; (b) HVR-L2 comprising SEQ ID NO: 10; and (c) HVR-L3 comprising SEQ ID NO: 11.

In some instances, the anti-human pro-epiregulin antibodies that bind to amino acid residues 148-169 of human pro-epiregulin include both VH and VL sequences having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequences of, the amino acid sequences of SEQ ID NOs: 16 and 17, respectively, and may or may not include post-translational modifications of those sequences.

In other instances, the invention provides antibodies that specifically bind human pro-epiregulin, wherein the antibodies include (a) an HVR-H1 comprising SEQ ID NO: 2; (b) an HVR-H2 comprising SEQ ID NO: 3; (c) an HVR-H3 comprising SEQ ID NO: 4; (d) an HVR-L1 comprising SEQ ID NO: 9; (e) an HVR-L2 comprising SEQ ID NO: 10; and (f) an HVR-L3 comprising SEQ ID NO: 11. In some instances, these anti-human pro-epiregulin antibodies include the following FRs: (a) FR-H1 comprising SEQ ID NO: 5; (b) FR-H2 comprising SEQ ID NO: 6; (c) FR-H3 comprising SEQ ID NO: 7; and (d) FR-H4 comprising SEQ ID NO: 8 and may additionally or alternatively include (e) FR-L1 comprising SEQ ID NO: 12; (f) FR-L2 comprising SEQ ID NO: 13; (g) FR-L3 comprising SEQ ID NO: 14; and (h) FR-L4 comprising SEQ ID NO: 15. In some embodiments, for example, the anti-human pro-epiregulin antibodies include both a VH and a VL sequence including the sequences of the amino acid sequences of SEQ ID NOs: 16 and 17, respectively, and may or may not include post-translational modifications.

For example, the invention features anti-human pro-epiregulin antibodies, such as the anti-human pro-epiregulin antibody J5H1L1, with the following heavy and light chain variable region sequences.

The amino acid sequence of the heavy chain variable region comprises the following:

(SEQ ID NO: 16)
QSVEESGGRLVTPGTPLTLTCTVSGFSLSRYGMSWVRQAPGKGLEYIG

SINRTAYTYYATWAKGRFTISRTSTTVDLRMTSLTTEDTATYFCARGL

TYGGSDYDYDDALWGPGTLVTVSS

The amino acid sequence of the light chain variable region comprises the following:

(SEQ ID NO: 17)
QVLTQTPSSVSAAVGGTVTINCQASQSVYKNKNLAWYQQKPGQPPKLLIY

RASTLASGVSSRFKGSGSGTQFTLTISGVQCADAATYYCQGEFSCSTFDC

ILFGGGTEMVVK.

In some instances, the anti-human pro-epiregulin antibodies that bind to amino acid residues 156-169 of human pro-epiregulin include at least one, two, three, four, five, or six HVRs selected from (a) HVR-H1 comprising SEQ ID NO: 18; (b) HVR-H2 comprising SEQ ID NO: 19; (c) HVR-H3 comprising SEQ ID NO: 20; (d) HVR-L1 comprising SEQ ID NO: 25 OR SEQ ID NO: 26; (e) HVR-L2 comprising SEQ ID NO: 27; and (f) HVR-L3 comprising SEQ ID NO: 28. For example, in some instances, the anti-human pro-epiregulin antibodies include (a) an HVR-H1 comprising SEQ ID NO: 18; (b) an HVR-H2 comprising SEQ ID NO: 19; and (c) an HVR-H3 comprising SEQ ID NO: 20. In some instances, the anti-human pro-epiregulin antibodies include (a) an HVR-L1 comprising SEQ ID NO: 25; (b) HVR-L2 comprising SEQ ID NO: 27; and (c) HVR-L3 comprising SEQ ID NO: 28. In some instances, the anti-human pro-epiregulin antibodies include (a) an HVR-L1 comprising SEQ ID NO: 26; (b) HVR-L2 comprising SEQ ID NO: 27; and (c) HVR-L3 comprising SEQ ID NO: 28.

In some instances wherein the anti-human pro-epiregulin antibodies bind to amino acid residues 156-169 of human pro-epiregulin and include (a) an HVR-H1 comprising SEQ ID NO: 18; (b) an HVR-H2 comprising SEQ ID NO: 19; and (c) an HVR-H3 comprising SEQ ID NO: 20, the anti-human pro-epiregulin antibodies further include the following heavy chain variable domain framework regions (FRs): (a) FR-H1 comprising SEQ ID NO: 21; (b) FR-H2 comprising SEQ ID NO: 22; (c) FR-H3 comprising SEQ ID NO: 23; or (d) FR-H4 comprising SEQ ID NO: 24. In some instances wherein the anti-human pro-epiregulin antibodies bind to amino acid residues 156-169 of human pro-epiregulin and include (a) an HVR-H1 comprising SEQ ID NO: 18; (b) an HVR-H2 comprising SEQ ID NO: 19; and (c) an HVR-H3 comprising SEQ ID NO: 20, the anti-human pro-epiregulin antibodies further include the following heavy chain variable domain framework regions (FRs): (a) FR-H1 comprising SEQ ID NO: 21; (b) FR-H2 comprising SEQ ID NO: 22; (c) FR-H3 comprising SEQ ID NO: 23; and (d) FR-H4 comprising SEQ ID NO: 24.

In some instances wherein the anti-human pro-epiregulin antibodies bind to amino acid residues 156-169 of human proepiregulin, the antibodies include (a) an HVR-H1 comprising SEQ ID NO: 18; (b) an HVR-H2 comprising SEQ ID NO: 19; (c) an HVR-H3 comprising SEQ ID NO: 20; (d) an HVR-L1 comprising SEQ ID NO: 25; (e) an HVR-L2 comprising SEQ ID NO: 27; and (f) an HVR-L3 comprising SEQ ID NO: 28. In some instances, these anti-human pro-epiregulin antibodies include the following FRs: (a) FR-H1 comprising SEQ ID NO: 21; (b) FR-H2 comprising SEQ ID NO: 22; (c) FR-H3 comprising SEQ ID NO: 23; and (d) FR-H4 comprising SEQ ID NO: 24 and may additionally or alternatively include (e) FR-L1 comprising SEQ ID NO: 29; (f) FR-L2 comprising SEQ ID NO: 30; (g) FR-L3 comprising SEQ ID NO: 31; and (h) FR-L4 comprising SEQ ID NO: 32.

In some instances wherein the anti-human pro-epiregulin antibodies bind to amino acid residues 156-169 of human proepiregulin, the antibodies include (a) an HVR-H1 comprising SEQ ID NO: 18; (b) an HVR-H2 comprising SEQ ID NO: 19; (c) an HVR-H3 comprising SEQ ID NO: 20; (d) an HVR-L1 comprising SEQ ID NO: 26; (e) an HVR-L2 comprising SEQ ID NO: 27; and (f) an HVR-L3 comprising SEQ ID NO: 28. In some instances, these anti-human pro-epiregulin antibodies include the following FRs: (a) FR-H1 comprising SEQ ID NO: 21; (b) FR-H2 comprising SEQ ID NO: 22; (c) FR-H3 comprising SEQ ID NO: 23; and (d) FR-H4 comprising SEQ ID NO: 24 and may additionally or alternatively include (e) FR-L1 comprising SEQ ID NO: 29; (f) FR-L2 comprising SEQ ID NO: 30; (g) FR-L3 comprising SEQ ID NO: 31; and (h) FR-L4 comprising SEQ ID NO: 32.

In some instances, the anti-human pro-epiregulin antibodies that bind to amino acid residues 156-169 of human pro-epiregulin may also include a heavy chain variable domain (VH) sequence having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 33. In certain embodiments, a VH sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 33), but an anti-human pro-epiregulin antibody including that sequence retains the ability to bind to human pro-epiregulin. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 33. In certain embodiments, substitutions, insertions, or deletions occur in regions outside the HVRs (i.e., in the FRs). Optionally, the anti-human pro-epiregulin antibodies include the VH sequence in SEQ ID NO: 33, including post-translational modifications of that sequence. In a particular embodiment, the VH comprises one, two, or three HVRs selected from: (a) HVR-H1 comprising SEQ ID NO: 18, (b) HVR-H2 comprising SEQ ID NO: 19, and (c) HVR-H3 comprising SEQ ID NO: 20.

In some instances, the anti-human pro-epiregulin antibodies that bind to amino acid residues 156-169 of human pro-epiregulin may also include a light chain variable domain (VL) having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 34 or SEQ ID NO: 35. In certain embodiments, a VL sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 34 or SEQ ID NO: 35), but an anti-human pro-epiregulin antibody including that sequence retains the ability to bind to human pro-epiregulin. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 34 or SEQ ID NO: 35. In certain embodiments, the substitutions, insertions, or deletions occur in regions outside the HVRs (i.e., in the FRs). Optionally, the anti-human pro-epiregulin antibody comprises the VL sequence in SEQ ID NO: 34 or SEQ ID NO: 35, including post-translational modifications of that sequence. In a particular embodiment, the VL comprises one, two or three HVRs selected from (a) HVR-L1 comprising SEQ ID NO: 25 or SEQ ID NO: 26; (b) HVR-L2 comprising SEQ ID NO: 27; and (c) HVR-L3 comprising SEQ ID NO: 28.

In some instances, the anti-human pro-epiregulin antibodies that bind to amino acid residues 156-169 of human pro-epiregulin include both VH and VL sequences having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequences of, the amino acid sequences of SEQ ID NOs: 17 and 18, respectively, and may or may not include post-translational modifications of those sequences.

In other instances, the invention provides antibodies that specifically bind human pro-epiregulin, wherein the antibodies include (a) an HVR-H1 comprising SEQ ID NO: 18; (b) an HVR-H2 comprising SEQ ID NO: 19; (c) an HVR-H3 comprising SEQ ID NO: 20; (d) an HVR-L1 comprising SEQ ID NO: 25; (e) an HVR-L2 comprising SEQ ID NO: 27; and (f) an HVR-L3 comprising SEQ ID NO: 28. In some instances, these anti-human pro-epiregulin antibodies include the following FRs: (a) FR-H1 comprising SEQ ID NO: 21; (b) FR-H2 comprising SEQ ID NO: 22; (c) FR-H3 comprising SEQ ID NO: 23; and (d) FR-H4 comprising SEQ ID NO: 24 and may additionally or alternatively include (e) FR-L1 comprising SEQ ID NO: 29; (f) FR-L2 comprising SEQ ID NO: 30; (g) FR-L3 comprising SEQ ID NO: 31; and (h) FR-L4 comprising SEQ ID NO: 32. In some embodiments, for example, the anti-human pro-epiregulin antibodies include both a VH and a VL sequence including the sequences of the amino acid sequences of SEQ ID NOs: 17 and 18, respectively, and may or may not include post-translational modifications. In some embodiments, for example, the anti-human pro-epiregulin antibodies include both a VH and a VL sequence including the sequences of the amino acid sequences of SEQ ID NOs: 17 and 19, respectively, and may or may not include post-translational modifications.

For example, the invention features anti-human pro-epiregulin antibodies, such as the anti-human pro-epiregulin antibody J89H12L3, with the following heavy and light chain variable region sequences:

The amino acid sequence of the heavy chain variable region comprises the following:

(SEQ ID NO: 33)
KSVEESGGRLVTPGTPLTLTCTVSGIDLSTFAMAWVRQAPGKGLEYIGFI

SLSDATYYATWAKGRFTISKSSSTTVDLKIITPTAEDTATYFCARVVGDS

SGYPNTFHPWGPGTLVTVSS

The amino acid sequence of the light chain variable region comprises the following:

(SEQ ID NO: 34)
QVLTQTPSPVSAAVGGTVTINCQASQSIHNSDFLAWYQQKPGQPPKLLIY

RASKLPSGVPSRFKGSGSGTQFTLTISDLECDDAATYYCQGTYYSGGWYF

TFGGGTEVVVK.

For another example, the invention features anti-human pro-epiregulin antibodies, such as the anti-human pro-epiregulin antibody J89H12L8, with the following heavy and light chain variable region sequences:

The amino acid sequence of the heavy chain variable region comprises the following:

(SEQ ID NO: 33)
KSVEESGGRLVTPGTPLTLTCTVSGIDLSTFAMAWVRQAPGKGLEYIGFI

SLSDATYYATWAKGRFTISKSSSTTVDLKIITPTAEDTATYFCARVVGDS

SGYPNTFHPWGPGTLVTVSS

The amino acid sequence of the light chain variable region comprises the following:

(SEQ ID NO: 35)
QVLTQTPSPVSAAVGGTVTINCQASQNIHNSDFLAWYQQKPGQPPKLLIY

RASKLPSGVPSRFKGSGSGTQFTLTISDLECDDAATYYCQGTYYSGGWYF

TFGGGTEVVVK.

In some instances, anti-human pro-epiregulin antibodies of the invention are antibodies that compete for binding to human pro-epiregulin with any one or more of the anti-human pro-epiregulin antibodies described above. In some instances, anti-human pro-epiregulin antibodies of the invention are antibodies that bind to the same epitope or substantially the same epitope as any one or more of the anti-human pro-epiregulin antibodies described above.

In some instances, an anti-human pro-epiregulin antibody according to any of the above embodiments may be a monoclonal antibody, comprising a chimeric, humanized, or human antibody. In one embodiment, an anti-human pro-epiregulin antibody is an antibody fragment, for example, a Fv, Fab, Fab', scFv, diabody, or F(ab')$_2$ fragment. In another embodiment, the antibody is a full-length antibody, e.g., an intact IgG antibody (e.g., an intact IgG1 antibody) or other antibody class or isotype as defined herein.

It should be understood that the anti-human pro-epiregulin antibodies of the invention, although useful for the detection of the presence or the expression level of human pro-epiregulin in a biological sample as exemplified by the Examples below, may also be used or adapted for therapeutic use.

In further aspects, the anti-human pro-epiregulin antibodies according to any of the above embodiments may incorporate any of the features, singly or in combination, as described in Sections 1-5 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293: 865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57: 4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20™) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al. *J. Mol. Biol.* 293: 865-881, 1999. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9: 129-134, 2003. For a review of scFv fragments, see, e.g., Pluckthun. *The Pharmacology of Monoclonal Antibodies*. Vol. 113, pp. 269-315, Rosenburg and Moore eds. Springer-Verlag, New York, 1994; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9: 129-134, 2003; and Hollinger et al. *Proc. Natl. Acad. Sci. USA.* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA.* 81: 6851-6855, 1984. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro et al. *Front. Biosci.* 13: 1619-1633, 2008, and are further described, e.g., in Riechmann et al. *Nature.* 332: 323-329, 1988; Queen et al. *Proc. Natl. Acad. Sci. USA.* 86: 10029-10033, 1989; U.S. Pat. Nos. 5,821,337, 7,527,791, 6,982,321, and 7,087,409; Kashmiri et al. *Methods.* 36: 25-34, 2005 (describing SDR (a-CDR) grafting); Padlan. *Mol. Immunol.* 28: 489-498, 1991 (describing "resurfacing"); DaU'Acqua et al. *Methods.* 36: 43-60, 2005 (describing "FR shuffling"); and Osbourn et al. *Methods* 36: 61-68, 2005 and Klimka et al. *Br. J. Cancer.* 83: 252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151: 2296, 1993); framework regions derived from the consensus sequence of human antibodies of a particular subgroup of light or heavy chain variable regions (see, e.g., Carter et al. *Proc. Natl. Acad. Sci. USA.* 89: 4285, 1992; and Presta et al. *J. Immunol.* 151: 2623, 1993); human mature (somatically mutated) framework regions or human germline framework regions (see, e.g., Almagro et al. *Front. Biosci.* 13: 1619-1633, 2008); and framework regions derived from screening FR libraries (see, e.g., Baca et al. *J. Biol. Chem.* 272: 10678-10684, 1997 and Rosok et al. *J. Biol. Chem.* 271: 22611-22618, 1996).

4. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for human pro-epiregulin and the other is for any other antigen. In certain embodiments, bispecific antibodies may bind to two different epitopes of human pro-epiregulin. Bispecific antibodies may also be used to localize cytotoxic agents to cells which express human pro-epiregulin. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein et al. *Nature.* 305: 537, 1983, WO 93/08829, and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. *Science.* 229: 81, 1985); using leucine zippers to produce bispecific antibodies (see, e.g., Kostelny et al. *J. Immunol.* 148(5): 1547-1553, 1992); using "diabody" technology for making bispecific antibody fragments (see, e.g., Hollinger et al. *Proc. Natl. Acad. Sci. USA.,* 90: 6444-6448, 1993); and using single-chain Fv (sFv) dimers (see, e.g. Gruber et al. *J. Immunol.* 152: 5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g. US 2006/0025576A1). The antibody or fragment herein also includes a "Dual Acting FAb" or "DAF" comprising an antigen binding site that binds to human pro-epiregulin as well as another, different antigen (see, e.g., US 2008/0069820).

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury. *Methods Mol. Biol.* 207: 179-196, 2008), and/or SDRs (a-CDRs), with the resulting variant VH or VL being tested for binding affinity. Affinity maturation by constructing and reselecting from secondary libraries has been described, e.g., in Hoogenboom et al. *Methods in Molecular Biology.* 178: 1-37, O'Brien et al. eds., Human Press, Totowa, N.J., 2001. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science.* 244: 1081-1085, 1989. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH.* 15: 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249, 2004; and Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249: 533-545, 1986; US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an anti-human pro-epiregulin antibody of the invention (e.g., J5-H1L1) provided herein, thereby generating an Fc region variant. The Fc region variant may comprise a human Fc region sequence (e.g., a human $IgG_1$, $IgG_2$, $IgG_3$ or $IgG_4$ Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch et al. *Annu. Rev. Immunol.* 9: 457-492, 1991. Non-limiting examples of in vitro assays to assess ADCC activity of a molecule of interest is described in U.S. Pat. Nos. 5,500,362 and 5,821, 337; Hellstrom et al. *Proc. Natl. Acad. Sci. USA.* 83: 7059-7063, 1986; Hellstrom et al. *Proc. Natl Acad. Sci. USA.* 82: 1499-1502, 1985; and Bruggemann et al. *J. Exp. Med.* 166: 1351-1361, 1987. Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Natl. Acad. Sci. USA.* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods.* 202: 163, 1996; Cragg et al. *Blood.* 101: 1045-1052, 2003; and Cragg et al. *Blood* 103: 2738-2743, 2004. FcRn binding and in vivo clearance/half life determinations can also be performed using methods known in the art (see, e.g., Petkova et al. *Intl. Immunol.* 18(12): 1759-1769, 2006).

Antibodies with reduced effector function include those with substitution of one or more of Fc region residues 238, 265, 269, 270, 297, 327, and 329 (U.S. Pat. No. 6,737,056). Such Fc mutants include Fc mutants with substitutions at two or more of amino acid positions 265, 269, 270, 297, and 327, including the so-called "DANA" Fc mutant with substitution of residues 265 and 297 to alanine (U.S. Pat. No. 7,332,581).

Certain antibody variants with improved or diminished binding to FcRs are described. See, e.g., U.S. Pat. No. 6,737,056; WO 2004/056312; and Shields et al. *J. Biol. Chem.* 9(2): 6591-6604, 2001.

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117: 587, 1976 and Kim et al, *J. Immunol.* 24: 249, 1994), are described in US Patent Application No. 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826). See also Duncan et al. *Nature.* 322:738-740, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

e) Antibody Derivatives

In certain embodiments, an anti-human pro-epiregulin antibody of the invention (e.g., J5-H1L1) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA.* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Exemplary Anti-Human Amphiregulin Antibodies

The invention provides anti-human amphiregulin antibodies useful for, e.g., diagnostic applications (e.g., immunohistochemistry (IHC), immunofluorescence (IF), and immunoblot (e.g., Western blot)). In one example, the invention provides anti-human amphiregulin antibodies that bind to an epitope including amino acid residues 238-252 of human amphiregulin (e.g., amino acid residues 238-252 of SEQ ID NO: 36), which is located at the carboxy terminus of the amphiregulin molecule. The epitope on human amphiregulin may be recognized in a manner that is conformation-dependent or conformation-independent.

In some instances, the anti-human amphiregulin antibodies that bind to amino acid residues 148-169 of human proepiregulin include at least one, two, three, four, five, or six HVRs selected from (a) HVR-H1 comprising SEQ ID NO: 37; (b) HVR-H2 comprising SEQ ID NO: 38; (c) HVR-H3 comprising SEQ ID NO: 39; (d) HVR-L1 comprising SEQ ID NO: 44; (e) HVR-L2 comprising SEQ ID NO: 45; and (f) HVR-L3 comprising SEQ ID NO: 46. For example, in some instances, the anti-human amphiregulin antibodies include (a) an HVR-H1 comprising SEQ ID NO: 37; (b) an HVR-H2 comprising SEQ ID NO: 38; and (c) an HVR-H3 comprising SEQ ID NO: 39. In some instances, the anti-human amphiregulin antibodies include (a) an HVR-L1 comprising SEQ ID NO: 44; (b) HVR-L2 comprising SEQ ID NO: 45; and (c) HVR-L3 comprising SEQ ID NO: 46.

In some instances wherein the anti-human amphiregulin antibodies bind to amino acid residues 238-252 of human amphiregulin and include (a) an HVR-H1 comprising SEQ ID NO: 37; (b) an HVR-H2 comprising SEQ ID NO: 38; and (c) an HVR-H3 comprising SEQ ID NO: 39, the anti-human amphiregulin antibodies further include the following heavy chain variable domain framework regions (FRs): (a) FR-H1 comprising SEQ ID NO: 40; (b) FR-H2 comprising SEQ ID NO: 41; (c) FR-H3 comprising SEQ ID NO: 42; or (d) FR-H4 comprising SEQ ID NO: 43. In some instances wherein the anti-human amphiregulin antibodies bind to amino acid residues 238-252 of human amphiregulin and include (a) an HVR-H1 comprising SEQ ID NO: 37; (b) an HVR-H2 comprising SEQ ID NO: 38; and (c) an HVR-H3 comprising SEQ ID NO: 39, the anti-human amphiregulin antibodies further include the following heavy chain variable domain framework regions (FRs): (a) FR-H1 comprising SEQ ID NO: 40; (b) FR-H2 comprising SEQ ID NO: 41; (c) FR-H3 comprising SEQ ID NO: 42; and (d) FR-H4 comprising SEQ ID NO: 43.

In some instances wherein the anti-human amphiregulin antibodies bind to amino acid residues 238-252 of human proepiregulin, the antibodies include (a) an HVR-H1 comprising SEQ ID NO: 37; (b) an HVR-H2 comprising SEQ ID NO: 38; (c) an HVR-H3 comprising SEQ ID NO: 39; (d) an HVR-L1 comprising SEQ ID NO: 44; (e) an HVR-L2 comprising SEQ ID NO: 45; and (f) an HVR-L3 comprising SEQ ID NO: 46. In some instances, these anti-human amphiregulin antibodies include the following FRs: (a) FR-H1 comprising SEQ ID NO: 40; (b) FR-H2 comprising SEQ ID NO: 41; (c) FR-H3 comprising SEQ ID NO: 42; and (d) FR-H4 comprising SEQ ID NO: 43 and may additionally or alternatively include (e) FR-L1 comprising SEQ ID NO: 47; (f) FR-L2 comprising SEQ ID NO: 48; (g) FR-L3 comprising SEQ ID NO: 49; and (h) FR-L4 comprising SEQ ID NO: 50.

In some instances, the anti-human amphiregulin antibodies that bind to amino acid residues 238-252 of human amphiregulin may also include a heavy chain variable domain (VH) sequence having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 51. In certain embodiments, a VH sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 51), but an anti-human amphiregulin antibody including that sequence retains the ability to bind to human amphiregulin. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 51. In certain embodiments, substitutions, insertions, or deletions occur in regions outside the HVRs (i.e., in the FRs). Optionally, the anti-human amphiregulin antibodies include the VH sequence in SEQ ID NO: 51, including post-translational modifications of that sequence. In a particular embodiment, the VH comprises one, two, or three HVRs selected from: (a) HVR-H1 comprising SEQ ID NO: 37, (b) HVR-H2 comprising SEQ ID NO: 38, and (c) HVR-H3 comprising SEQ ID NO: 39.

In some instances, the anti-human amphiregulin antibodies that bind to amino acid residues 238-252 of human amphiregulin may also include a light chain variable domain (VL) having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 52. In certain embodiments, a VL sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 52), but an anti-human amphiregulin antibody including that sequence retains the ability to bind to human amphiregulin. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 52. In certain embodiments, the substitutions, insertions, or deletions occur in regions outside the HVRs (i.e., in the FRs). Optionally, the anti-human amphiregulin antibody comprises the VL sequence in SEQ ID NO: 52, including post-translational modifications of that sequence. In a particular embodiment, the VL comprises one, two or three HVRs selected from (a) HVR-L1 comprising SEQ ID NO: 44; (b) HVR-L2 comprising SEQ ID NO: 45; and (c) HVR-L3 comprising SEQ ID NO: 46.

In some instances, the anti-human amphiregulin antibodies that bind to amino acid residues 238-252 of human amphiregulin include both VH and VL sequences having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequences of, the amino acid sequences of SEQ ID NOs: 16 and 17, respectively, and may or may not include post-translational modifications of those sequences.

In other instances, the invention provides antibodies that specifically bind human amphiregulin, wherein the antibodies include (a) an HVR-H1 comprising SEQ ID NO: 37; (b) an HVR-H2 comprising SEQ ID NO: 38; (c) an HVR-H3 comprising SEQ ID NO: 39; (d) an HVR-L1 comprising SEQ ID NO: 44; (e) an HVR-L2 comprising SEQ ID NO: 45; and (f) an HVR-L3 comprising SEQ ID NO: 46. In some instances, these anti-human amphiregulin antibodies include the following FRs: (a) FR-H1 comprising SEQ ID NO: 40; (b) FR-H2 comprising SEQ ID NO: 41; (c) FR-H3 comprising SEQ ID NO: 42; and (d) FR-H4 comprising SEQ ID NO: 43 and may additionally or alternatively include (e) FR-L1 comprising SEQ ID NO: 47; (f) FR-L2 comprising SEQ ID NO: 48; (g) FR-L3 comprising SEQ ID NO: 49; and (h) FR-L4 comprising SEQ ID NO: 50. In some embodiments, for example, the anti-human amphiregulin antibodies include both a VH and a VL sequence including the sequences of the amino acid sequences of SEQ ID NOs: 16 and 17, respectively, and may or may not include post-translational modifications.

For example, the invention features anti-human amphiregulin antibodies, such as the anti-human amphiregulin antibody J111H1L10, with the following heavy and light chain variable region sequences.

The amino acid sequence of the heavy chain variable region comprises the following:

(SEQ ID NO: 51)
QSLEESRGGLIKPGGTLTLTCTVSGFSLSSYAISWVRQAPGNGLEWIGFI

VGSSGSAYYASWAKSRSTITRDTNLNTVTLKMTSLTAADTATYFCAKGLY

SGGNYWGPGTLVTVSS

The amino acid sequence of the light chain variable region comprises the following:

(SEQ ID NO: 52)
AVLTQTPSPVSAAVGGTVSISCQSSQSVDENNYLSWFQQKPGQPPKLLIY

RASTLESGVPSRFSGSGSGTQFTLTVSGVQCDDAATYYCLGGYSGYSDDG

FGGGTEVVVK.

In some instances, anti-human amphiregulin antibodies of the invention are antibodies that compete for binding to human amphiregulin with any one or more of the anti-human amphiregulin antibodies described above. In some instances, anti-human amphiregulin antibodies of the invention are antibodies that bind to the same epitope or substantially the same epitope as any one or more of the anti-human amphiregulin antibodies described above.

In some instances, an anti-human amphiregulin antibody according to any of the above embodiments may be a monoclonal antibody, comprising a chimeric, humanized, or human antibody. In one embodiment, an anti-human amphiregulin antibody is an antibody fragment, for example, a Fv, Fab, Fab', scFv, diabody, or F(ab')$_2$ fragment. In another embodiment, the antibody is a full-length antibody, e.g., an intact IgG antibody (e.g., an intact IgG1 antibody) or other antibody class or isotype as defined herein.

It should be understood that the anti-human amphiregulin antibodies of the invention, although useful for the detection of the presence or the expression level of human amphiregulin in a biological sample as exemplified by the Examples below, may also be used or adapted for therapeutic use.

In further aspects, the anti-human amphiregulin antibodies according to any of the above embodiments may incorporate any of the features, singly or in combination, as described in Sections 1-5 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293: 865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57: 4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20™) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al. *J. Mol. Biol.* 293: 865-881, 1999. If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9: 129-134, 2003. For a review of scFv fragments, see, e.g., Pluckthun. *The Pharmacology of Monoclonal Antibodies.* Vol. 113, pp. 269-315, Rosenburg and Moore eds. Springer-Verlag, New York, 1994; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9: 129-134, 2003; and Hollinger et al. *Proc. Natl. Acad. Sci. USA.* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA.* 81: 6851-6855, 1984. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro et al. *Front. Biosci.* 13: 1619-1633, 2008, and are further described, e.g., in Riechmann et al. *Nature.* 332: 323-329, 1988; Queen et al. *Proc. Natl. Acad. Sci. USA.* 86: 10029-10033, 1989; U.S. Pat. Nos. 5,821,337, 7,527,791, 6,982,321, and 7,087,409; Kashmiri et al. *Methods.* 36: 25-34, 2005 (describing SDR (a-CDR) grafting); Padlan. *Mol. Immunol.* 28: 489-498, 1991 (describing "resurfacing"); DaU'Acqua et al. *Methods.* 36: 43-60, 2005 (describing "FR shuffling"); and Osbourn et al. *Methods* 36: 61-68, 2005 and Klimka et al. *Br. J. Cancer.* 83: 252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151: 2296, 1993); framework regions derived from the consensus sequence of human antibodies of a particular subgroup of light or heavy chain variable regions (see, e.g., Carter et al. *Proc. Natl. Acad. Sci. USA.* 89: 4285, 1992; and Presta et al. *J. Immunol.* 151: 2623, 1993); human mature (somatically mutated) framework regions or human germline framework regions (see, e.g., Almagro et al. *Front. Biosci.* 13: 1619-1633, 2008); and framework regions derived from screening FR libraries (see, e.g., Baca et al. *J. Biol. Chem.* 272: 10678-10684, 1997 and Rosok et al. *J. Biol. Chem.* 271: 22611-22618, 1996).

4. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for human amphiregulin and the other is for any other antigen. In certain embodiments, bispecific antibodies may bind to two different epitopes of human amphiregulin. Bispecific antibodies may also be used to localize cytotoxic agents to cells which express human amphiregulin. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein et al. *Nature.* 305: 537, 1983, WO 93/08829, and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. *Science.* 229: 81, 1985); using leucine zippers to produce bispecific antibodies (see, e.g., Kostelny et al. *J. Immunol.* 148(5): 1547-1553, 1992); using "diabody" technology for making bispecific antibody fragments (see, e.g., Hollinger et al. *Proc. Natl. Acad. Sci. USA.,* 90: 6444-6448, 1993); and using single-chain Fv (sFv) dimers (see, e.g. Gruber et al. *J. Immunol.* 152: 5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to human amphiregulin as well as another, different antigen (see, e.g., US 2008/0069820).

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury. *Methods Mol. Biol.* 207: 179-196, 2008), and/or SDRs (a-CDRs), with the resulting variant VH or VL being tested for binding affinity. Affinity maturation by constructing and reselecting from secondary libraries has been described, e.g., in Hoogenboom et al. *Methods in Molecular Biology.* 178: 1-37, O'Brien et al. eds., Human Press, Totowa, N.J., 2001. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science.* 244: 1081-1085, 1989. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH.* 15: 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249, 2004; and Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249: 533-545, 1986; US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an anti-human amphiregulin antibody of the invention (e.g., J111H1L10) provided herein, thereby generating an Fc region variant. The Fc region variant may comprise a human Fc region sequence (e.g., a human $IgG_1$, $IgG_2$, $IgG_3$ or $IgG_4$ Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch et al. *Annu. Rev. Immunol.* 9: 457-492, 1991. Non-limiting examples of in vitro assays to assess ADCC activity of a molecule of interest is described in U.S. Pat. Nos. 5,500,362 and 5,821,337; Hellstrom et al. *Proc. Natl. Acad. Sci. USA.* 83: 7059-7063, 1986; Hellstrom et al. *Proc. Natl Acad. Sci. USA.* 82: 1499-1502, 1985; and Bruggemann et al. *J. Exp. Med.* 166: 1351-1361, 1987. Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Natl. Acad. Sci. USA.* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods.* 202: 163, 1996; Cragg et al. *Blood.* 101: 1045-1052, 2003; and Cragg et al. *Blood* 103: 2738-2743, 2004. FcRn binding and in vivo clearance/half life determinations can also be performed using methods known in the art (see, e.g., Petkova et al. *Intl. Immunol.* 18(12): 1759-1769, 2006).

Antibodies with reduced effector function include those with substitution of one or more of Fc region residues 238, 265, 269, 270, 297, 327, and 329 (U.S. Pat. No. 6,737,056). Such Fc mutants include Fc mutants with substitutions at two or more of amino acid positions 265, 269, 270, 297, and 327, including the so-called "DANA" Fc mutant with substitution of residues 265 and 297 to alanine (U.S. Pat. No. 7,332,581).

Certain antibody variants with improved or diminished binding to FcRs are described. See, e.g., U.S. Pat. No. 6,737,056; WO 2004/056312; and Shields et al. *J. Biol. Chem.* 9(2): 6591-6604, 2001.

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117: 587, 1976 and Kim et al, *J. Immunol.* 24: 249, 1994), are described in US Patent Application No. 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826). See also Duncan et al. *Nature.* 322:738-740, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an anti-human amphiregulin antibody of the invention (e.g., J111H1L10) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA.* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

C. Recombinant Methods and Compositions

Antibodies may be produced using recombinant methods and compositions, e.g., as described in U.S. Pat. No. 4,816,567. In one embodiment, isolated nucleic acid encoding an anti-human pro-epiregulin antibody described herein (e.g., J5-H1L1, J89H12L3, and J89H12L8) or an anti-human amphiregulin (e.g. J111-H1L10) is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an anti-human pro-epiregulin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human pro-epiregulin antibody described herein (e.g., J5-H1L1, J89H12L3, and J89H12L8) or an anti-human amphiregulin (e.g. J111-H1L10), nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton. *Methods in Molecular Biology.* Vol. 248, pp. 245-254, B. K. C. Lo, ed., Humana Press, Totowa, N.J., 2003, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross. *Nat. Biotech*. 22: 1409-1414, 2004 and Li et al. *Nat. Biotech*. 24: 210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol*. 36:59, 1977); baby hamster kidney cells (BHK); mouse Sertoli cells (TM4 cells as described, e.g., in *Mather. Biol. Reprod*. 23:243-251, 1980); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather et al. *Annals N.Y. Acad. Sci*. 383:44-68, 1982; MRC 5 cells; and FS4 cells. Other useful mammalian host cell lines include Chinese hamster ovary (CHO) cells, including DHFR" CHO cells (Urlaub et al. *Proc. Natl. Acad. Sci. USA*. 77: 4216, 1980); and myeloma cell lines such as YO, NSO and Sp2/0. For a review of certain mammalian host cell lines suitable for antibody production, see, e.g., Yazaki et al. *Methods in Molecular Biology*. Vol. 248, pp. 255-268, B. K. C. Lo, ed., Humana Press, Totowa, N.J., 2003.

D. Assays

Anti-human pro-epiregulin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, immunohistochemistry, immunofluorescence, etc.

In another aspect, competition assays may be used to identify an antibody that competes with any one of the antibodies of the invention for binding to human pro-epiregulin (e.g., anti-human pro-epiregulin antibody J5H1L1, J89H12L3, and J89H12L8) or to amphiregulin (e.g. anti-human amphiregulin antibody J111H1L10). In certain embodiments, such a competing antibody binds to the same epitope (e.g., a linear or a conformational epitope) that is bound by any one of the antibodies of the invention (e.g., anti-human pro-epiregulin antibody J5H1L1, J89H12L3, or J89H12L8 or anti-human amphiregulin antibody J111H1L10). Detailed exemplary methods for mapping an epitope to which an antibody binds are provided in Morris "Epitope Mapping Protocols," in *Methods in Molecular Biology* Vol. 66 (Humana Press, Totowa, N.J., 1996).

In an exemplary competition assay, immobilized human pro-epiregulin is incubated in a solution comprising a first labeled antibody that binds to human pro-epiregulin (e.g., anti-human pro-epiregulin antibody J5H1L1, J89H12L3, and J89H12L8) and a second unlabeled antibody that is being tested for its ability to compete with the first antibody for binding to human pro-epiregulin. The second antibody may be present in a hybridoma supernatant. As a control, immobilized human pro-epiregulin is incubated in a solution comprising the first labeled antibody but not the second unlabeled antibody. After incubation under conditions permissive for binding of the first antibody to human pro-epiregulin, excess unbound antibody is removed, and the amount of label associated with immobilized human pro-epiregulin is measured. If the amount of label associated with immobilized human pro-epiregulin is substantially reduced in the test sample relative to the control sample, then that indicates that the second antibody is competing with the first antibody for binding to human pro-epiregulin. See, e.g., Harlow et al. *Antibodies: A Laboratory Manual*. Ch. 14 (Cold Spring Harbor Laboratory, Cold Spring Harbor, N.Y., 1988).

In another exemplary competition assay, immobilized human amphiregulin is incubated in a solution comprising a first labeled antibody that binds to human amphiregulin (e.g., anti-human amphiregulin antibody J111H1L10) and a second unlabeled antibody that is being tested for its ability to compete with the first antibody for binding to human amphiregulin. The second antibody may be present in a hybridoma supernatant. As a control, immobilized human amphiregulin is incubated in a solution comprising the first labeled antibody but not the second unlabeled antibody. After incubation under conditions permissive for binding of the first antibody to human amphiregulin, excess unbound antibody is removed, and the amount of label associated with immobilized human amphiregulin is measured. If the amount of label associated with immobilized human amphiregulin is substantially reduced in the test sample relative to the control sample, then that indicates that the second antibody is competing with the first antibody for binding to human amphiregulin. See, e.g., Harlow et al. *Antibodies: A Laboratory Manual*. Ch. 14 (Cold Spring Harbor Laboratory, Cold Spring Harbor, N.Y., 1988).

2. Detection Assays

In one aspect, assays are provided for identifying anti-human pro-epiregulin antibodies useful for detecting the presence of human pro-epiregulin, e.g., in immunohistochemistry (IHC) or immunofluorescence (IF) assays. In certain embodiments, an antibody of the invention is tested for such activity.

E. Immunoconjugates

The invention also provides immunoconjugates comprising an anti-human pro-epiregulin antibody herein conjugated to one or more labels and/or agents, such as radioactive isotopes.

In one embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an anti-human pro-epiregulin antibody and label or agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the label or agent. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

F. Methods and Compositions for Diagnostics and Detection

In certain embodiments, the anti-human pro-epiregulin antibodies provided herein are useful for detecting the presence of human pro-epiregulin in a biological sample. Likewise, the anti-human amphiregulin antibodies provided herein are useful for detecting the presence of human amphiregulin in a biological sample. The term "detecting" as used herein encompasses quantitative or qualitative detection.

In one instance, an anti-human pro-epiregulin antibody (e.g., J5-H1L1, J89H12L3, or J89H12L8) for use in a method of diagnosis or detection is provided. In one instance, for example, a method of detecting the presence of human pro-epiregulin in a biological sample, described below, is provided. In certain embodiments, the method comprises contacting the biological sample with an anti-human pro-epiregulin antibody as described herein under conditions permissive for binding of the anti-human pro-epiregulin antibody to human pro-epiregulin, and detecting whether a complex is formed between the anti-human pro-epiregulin antibody and human pro-epiregulin. Such method may be an in vitro or in vivo method. Anti-human pro-epiregulin antibodies of the invention (e.g., J5-H1L1, J89H12L3, or J89H12L8) can be used, for example, in immunoassays, including, for example, immunohistochemistry (IHC), immunofluorescence (IF), immunoblotting (e.g., Western blotting), flow cytometry, and Enzyme-linked Immunosorbant Assay (ELISA). In one embodiment, an anti-human pro-epiregulin antibody is used to select subjects eligible for therapy with an anti-human pro-epiregulin antibody, for example, where human pro-epiregulin is a biomarker for selection of patients.

In one instance, an anti-human amphiregulin antibody (e.g., J111H1L10) for use in a method of diagnosis or detection is provided. In one instance, for example, a method of detecting the presence of human amphiregulin in a biological sample, described below, is provided. In certain embodiments, the method comprises contacting the biological sample with an anti-human amphiregulin antibody as described herein under conditions permissive for binding of the anti-human amphiregulin antibody to human amphiregulin, and detecting whether a complex is formed between the anti-human amphiregulin antibody and human amphiregulin. Such method may be an in vitro or in vivo method. Anti-human amphiregulin antibodies of the invention (e.g., J111H1L10) can be used, for example, in immunoassays, including, for example, immunohistochemistry (IHC), immunofluorescence (IF), immunoblotting (e.g., Western blotting), flow cytometry, and Enzyme-linked Immunosorbant Assay (ELISA). In one embodiment, an anti-human amphiregulin antibody is used to select subjects eligible for therapy with an anti-human amphiregulin antibody, for example, where human amphiregulin is a biomarker for selection of patients.

In certain instances, labeled anti-human pro-epiregulin and/or anti-human amphiregulin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, for example, through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

It is also understood that any of the above methods for diagnosis and/or detection may be carried out using an immunoconjugate of the invention, as described above, in place of or in addition to an unconjugated anti-human pro-epiregulin or anti-human amphiregulin antibody.

G. Biological Samples

In certain embodiments, the anti-human pro-epiregulin and/or anti-human amphiregulin antibodies of the invention (e.g., J5H1L1, J89H12L3, J89H12L8 and/or J111H1L10) can be used to detect the presence of human pro-epiregulin and/or human amphiregulin in biological samples using methods known in the art or described herein.

In some instances a biological sample includes a tissue or a cell sample. For example, a biological sample may include a cell or tissue from normal or cancer patients, such as, for example, normal and cancerous tissue of breast, colon, lung, kidney, bone, brain, muscle, stomach, pancreas, bladder, ovary, uterus, as well as heart, embryonic, and placental tissue.

In certain instances the source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments the biological sample is obtained from in vitro tissue or cell culture. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded (FFPE) tumor samples or frozen tumor samples.

In some embodiments the biological sample contains compounds which are not naturally intermixed with the tissue in nature such as preservatives, anticoagulants, buffers, nutrients, antibiotics, or the like. In certain embodiments the biological sample has been exposed to and/or contains one or more fixatives. Fixatives that can be used with methods and compositions of the invention include formalin, glutaraldehyde, osmium tetraoxide, acetic acid, ethanol, acetone, picric acid, chloroform, potassium dichromate and mercuric chloride and/or stabilizing by microwave heating or freezing.

In some embodiments, the biological sample is from a subject having, predisposed to, or being tested for an autoimmune disease. In certain embodiments, the autoimmune disease is an autoimmune rheumatologic disorder (including rheumatoid arthritis, Sjogren's syndrome, scleroderma, lupus such as SLE and lupus nephritis, polymyositis-dermatomyositis, cryoglobulinemia, anti-phospholipid antibody syndrome, and psoriatic arthritis), an autoimmune gastrointestinal and liver disorder (including inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (including ANCA-negative vasculitis and ANCA-associated vasculitis, including Churg-Strauss vasculitis, Wegener's granulomatosis, and microscopic polyangiitis), an autoimmune neurological disorder (including multiple sclerosis, opsoclonus myoclonus syndrome, myasthenia gravis, neuromyelitis optica, Parkinson's disease, Alzheimer's disease, and autoimmune polyneuropathies), a renal disorder (including glomerulonephritis, Goodpasture's syndrome, and Berger's disease), an autoimmune dermatologic disorder (including psoriasis, urticaria, hives, pemphigus vulgaris, bullous pemphigoid, and cutaneous lupus erythematosus), a hematologic disorder (including thrombocytopenic purpura, thrombotic thrombocytopenic purpura, post-transfusion purpura, and autoimmune hemolytic anemia), atherosclerosis, uveitis, an autoimmune hearing disease (including inner ear disease and hearing loss), Behcet's disease, Raynaud's syndrome, organ transplant, or an autoimmune endocrine disorder (including diabetic-related autoimmune diseases such as insulin-dependent diabetes mellitus (IDDM), Addison's disease, and autoimmune thyroid disease (including Graves' disease and thyroiditis)).

In other embodiments, the biological sample is from a subject having, predisposed to, or being tested for cancer. In certain embodiments the cancer is carcinoma, lymphoma (including Hodgkin's and non-Hodgkin's lymphoma), blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, or various types of head and neck cancer. In one specific example, the biological sample is a colorectal tumor sample

III. Examples

The following are examples of methods and compositions of the invention. It is understood that various other embodiments may be practiced, given the general description provided above.

Rabbit monoclonal antibodies were raised against synthetic peptides corresponding to the C-terminus of human precursor EREG/AREG proteins. As a result, these antibodies detect the membrane-bound forms of pro-EREG and pro-AREG proteins prior to their cleavage but also detect the cytosolic fragment of the precursor proteins prior to being transported to the cell membrane.

Example 1. Generation of Anti-Human
Pro-Epiregulin Antibodies Against Amino Acids
148-169 of SEQ ID NO: 1

Anti-human pro-epiregulin rabbit monoclonal antibodies were generated as schematically depicted in FIG. 1.

Briefly, the peptide fragment of amino acid residues 148-169 of SEA) ID NO: 1 was synthesized and conjugated via glutaraldehyde to keyhole limpet hemocyanin (KLH), an extensively used carrier protein for stimulating a substantial immune response via antibody production. New Zealand White rabbits were immunized with KLH conjugated human pro-epiregulin antigen emulsified with complete Freund's adjuvant followed by a series of human pro-epiregulin antigen booster emulsified with incomplete Freund's adjuvant. The antibody-expressing cells were screened by enzyme-linked immunoabsorbant assay (ELISA) using the human pro-epiregulin antigen. All ELISA positive clones were further screened by immunohistochemistry (IHC), and the clone producing the antibody with the highest specificity was selected. For recombinant production of anti-human pro-epiregulin antibodies, cDNA coding for the heavy chain and light chain sequences of the antibodies were cloned, expressed by co-transfection, and screened for binding to human pro-epiregulin by IHC. Anti-human pro-epiregulin monoclonal antibody J5H1L1 was produced using these methods and subsequently purified by Protein A affinity chromatography. The heavy and light chain variable region sequences of the J5-H1L1 antibody are as follows.

The amino acid sequence of the heavy chain variable region comprises the following:

```
                                    (SEQ ID NO: 16)
QSVEESGGRLVTPGTPLTLTCTVSGFSLSRYGMSWVRQAPGKGLEYIGSI

NRTAYTYYATWAKGRFTISRTSTTVDLRMTSLTTEDTATYFCARGLTYGG

SDYDYDDALWGPGTLVTVSS
```

The amino acid sequence of the light chain variable region comprises the following:

(SEQ ID NO: 17)
QVLTQTPSSVSAAVGGTVTINCQASQSVYKNKNLAWYQQKPGQPPKLLIY
RASTLASGVSSRFKGSGSGTQFTLTISGVQCADAATYYCQGEFSCSTFDC
ILFGGGTEMVVK.

Example 2. Generation of Anti-Human Amphiregulin Antibodies

Anti-human amphiregulin rabbit monoclonal antibodies were generated as schematically depicted in FIG. 1. Briefly, the peptide fragment of amino acid residues 238-252 of SEQ ID NO: 36 was synthesized and conjugated via glutaraldehyde to keyhole limpet hemocyanin (KLH), an extensively used carrier protein for stimulating a substantial immune response via antibody production. New Zealand White rabbits were immunized with KU-11 conjugated human amphiregulin antigen emulsified with complete Freund's adjuvant followed by a series of human amphiregulin antigen booster emulsified with incomplete Freund's adjuvant. The antibody-expressing cells were screened by enzyme-linked immunoabsorbant assay (ELISA) using the human amphiregulin antigen. All ELISA positive clones were further screened by immunohistochemistry (IHC), and the clone producing the antibody with the highest specificity was selected. For recombinant production of anti-human amphiregulin antibodies, cDNA coding for the heavy chain and light chain sequences of the antibodies were cloned, expressed by co-transfection, and screened for binding to human amphiregulin by IHC. Anti-human amphiregulin monoclonal antibody J111H1L10 was produced using these methods and subsequently purified by Protein A affinity chromatography. The heavy and light chain variable region sequences of the J111H1L10 antibody are as follows.

The amino acid sequence of the heavy chain variable region comprises the following:

(SEQ ID NO: 51)
QSLEESRGGLIKPGGTLTLTCTVSGFSLSSYAISWVRQAPGNGLEWIGFI
VGSSGSAYYASWAKSRSTITRDTNLNTVTLKMTSLTAADTATYFCAKGLY
SGGNYWGPGTLVTVSS

The amino acid sequence of the light chain variable region comprises the following:

(SEQ ID NO: 52)
AVLTQTPSPVSAAVGGTVSISCQSSQSVDENNYLSWFQQKPGQPPKLLIY
RASTLESGVPSRFSGSGSGTQFTLTVSGVQCDDAATYYCLGGYSGYSDDG
FGGGTEVVVK.

Example 3. Immunohistochemical Assays Using Anti-Human Pro-Epiregulin and Anti-Human Amphiregulin Antibodies Reagents All assay optimization were performed on human non-small cell lung carcinoma (NSCLC) (NCI-H1975; NCI-H1650; H460; NCI-HCC827; H2228; Calu-3; H820), breast (MCF7; A431) carcinoma cell lines and colorectal cancer tissues. Stained slides for the tested conditions were evaluated by a trained pathologist and the optimal staining conditions were determined based on the staining intensity, percentage of positive cells and the level of non-specific (background) staining. The examined and the nominal conditions (bold) developed for EREG/AREG IHC is shown in Table 3.

TABLE 3

The examined and the nominal assay conditions (bold) for EREG/AREG IHC assays

| Procedure | XT OptiView DAB IHC | | | | | | |
|---|---|---|---|---|---|---|---|
| Antibody | EREG D4O5I | EREG S17H9L6 | EREG J59H1L2 | EREG J23H3.12L7 | EREG J5H1L1 | AREG J13H2L6 | AREG J111H1L10 |
| Sample Type | Carcinoma cell lines; Colorectal cancer cases | | | | | | |
| Paraffin | Selected | | | | | | |
| De-paraffinization | Selected | | | | | | |
| Cell Conditioning | CC1: 32 min | CC1: 0-32-64-92 min CC2: 8-16-32 min | CC1: 0-32-64-92 min CC2: 8-16-32 min | CC1: 32-64-92 min | CC1: 16-32-48-64-92 min | CC1: 0-32-64-92 min CC2: 8-16-32 min | CC1: 32-48-64-80 min |
| Peroxidase inhibition | Pre-peroxidase selected | Pre-peroxidase selected | Pre-peroxidase selected | Post-peroxidase selected | Post-peroxidase selected | Pre-peroxidase selected | Pre-peroxidase selected |
| Primary Ab Concentration (μg/ml) | 2 | 0.5; 1; 5; 7.5; 10; 15; 20; 25; 30; 50; 100 | 0.1; 0.5; 1; 2.5; 5; 10; 20; 25; 50; 100 | 0.1; 0.25; 0.5; 1; 2.5; 5; 10 | 0.5-1-2.5-3-5-10-25-50 | 0.1; 0.5; 1; 2; 3; 4; 5; 7.5; 10; | 0.1; 0.5; 1; 2; 5; 10; 25; 50 |
| Ab Diluent | 95028 | 90039 | 90040 | 95119 | 95119 | 90103 | 95119 |
| Primary Ab Temperature | 37° C. | No heat; 37° C.; 42° C. | No heat; 37° C.; 42° C. | No heat; 37° C.; 42° C. | No heat; 37° C.; 42° C. | No heat; 37° C.; 42° C. | No heat; 37° C.; 42° C. |
| Primary Ab Incubation | 16 min | 8-12-16-20-24 min | 16 min | 16-20-24 min | 16-20-24 min | 8-16-20-24-28-32-60 | 8-12-16 min |
| Amplify | Not Selected | Selected (4/4) | Not selected | Not Selected | Not Selected | Not Selected | Not Selected |
| Counterstain | Hematoxylin II, 4 min Bluing reagent, 4 min | | | | | | |

TABLE 3-continued

The examined and the nominal assay conditions (bold) for EREG/AREG IHC assays

| Staining Result | Good staining | Less sensitive; non-specific staining in stroma and normal colon | Less sensitive non-specific staining in nucleus; stroma and normal colon | Good sensitivity but high non-specific staining in testis | The best quality staining | Good staining but low sensitivity | The best quality staining |
|---|---|---|---|---|---|---|---|

Figure 2:
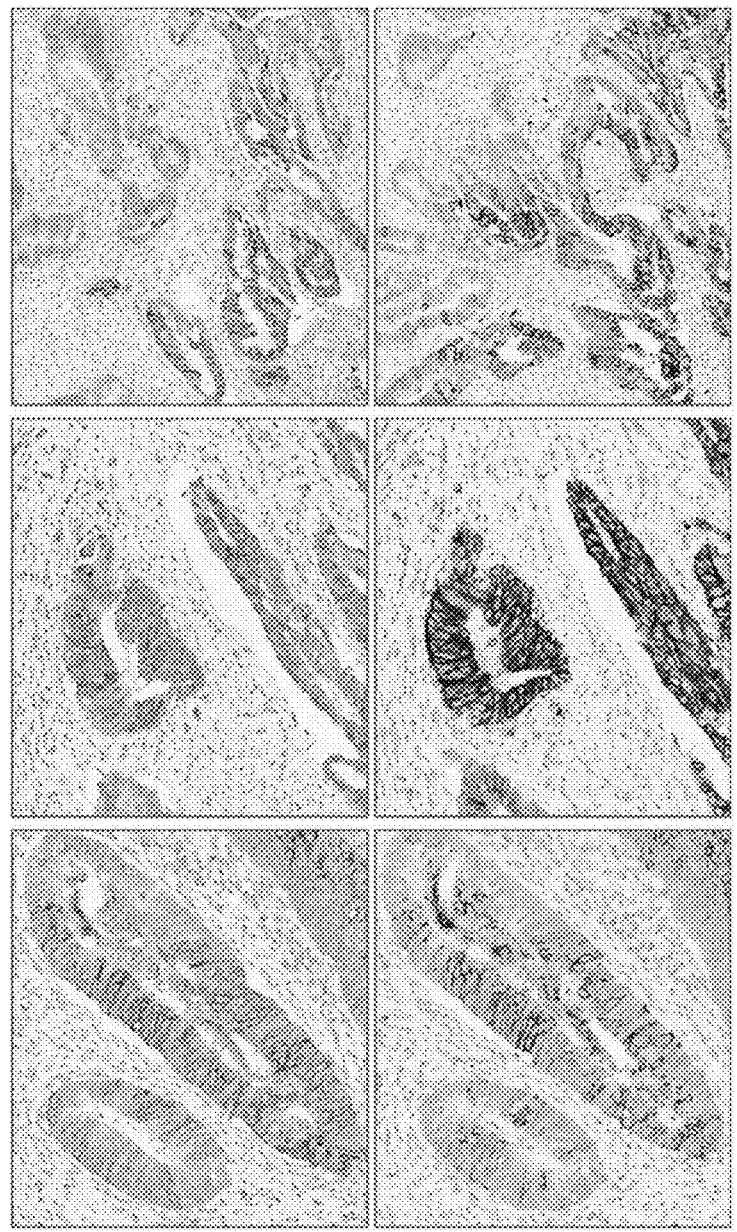
FIG. 2 is an image showing the results of immunohistochemistry (IHC) on formalin-fixed, paraffin-Embedded (FFPE) colon cancer tissue comparing clone J5H1L1 to a commercially available clone from Cell Signaling Technologies, Inc.

Of the six anti-EREG rabbit monoclonal antibodies, clone D4O5I obtained from CST and clone J5H1L1 developed by Spring Bioscience provided acceptable staining. Although both EREG clones showed similar specificity, anti-EREG clone J5H1L1 was more sensitive (FIG. 2). EREG protein expression was mainly found in tumor cells but clone J5H1L1 was able to detect basal level of expression in normal colonic epithelium as well.

Figure 3:
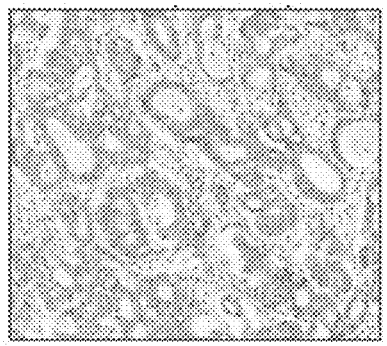
FIG. 3 is an image of an IHC assay using two clones of anti-human amphiregulin antibodies to stain formalin-fixed, paraffin embedded metastatic colorectal cancer tissue.
Figure 3:
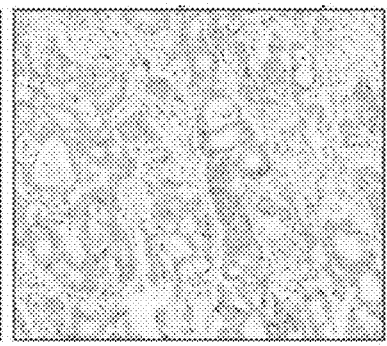
Figure 3:
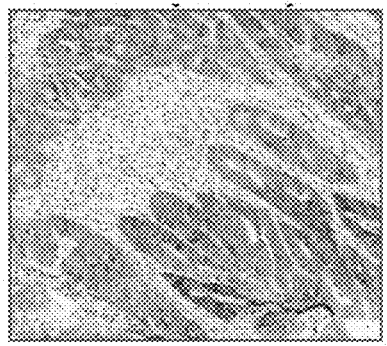
Figure 3:
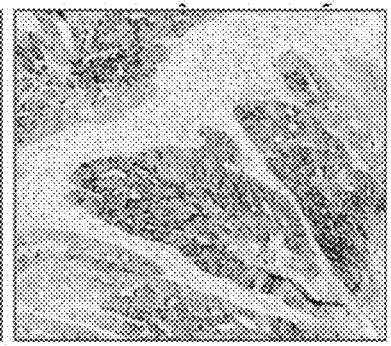

Similar to EREG IHC, AREG immunohistochemistry showed varying levels of protein expression in tumor cells and weak expression in normal colon. Of the two AREG rabbit monoclonal antibodies, clone J111H1L10 performed better by being more sensitive and more specific compared to clone J13H2L6. FIG. 3 represents images for the AREG IHC staining in colon cancers.

Figure 4A:
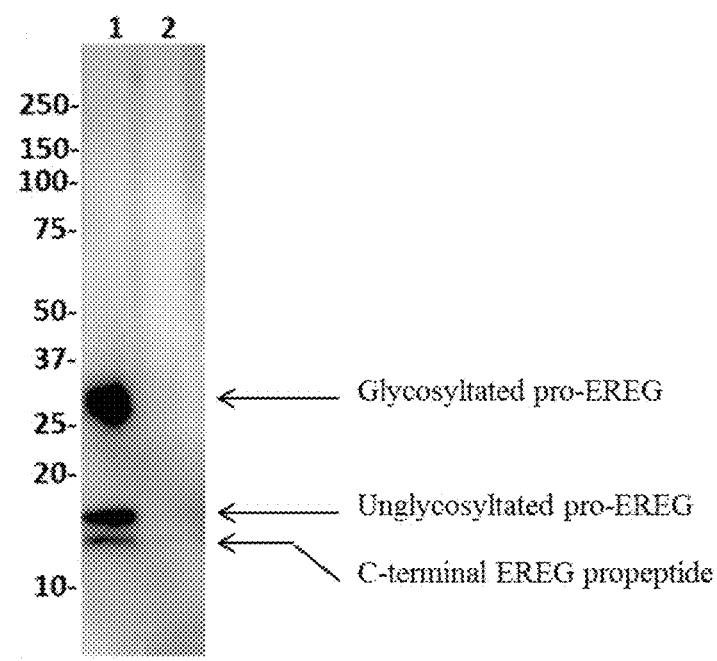
FIG. 4A is an image showing the results of a Western blot of EREG.
Figure 4B:
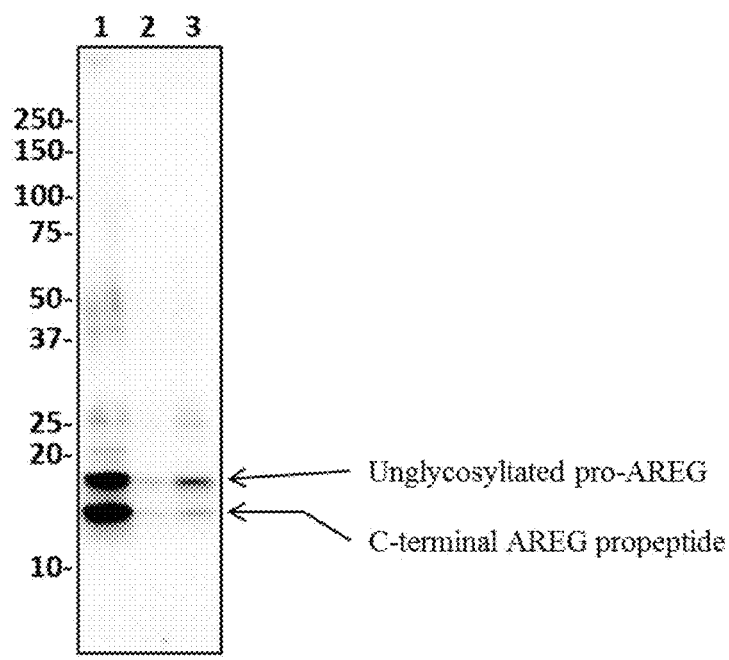
FIG. 4B is an image showing the results of a Western blot of AREG.

Specificity of EREG/AREG antibodies was tested by Western-blot analysis of extracts from various control cell lines. FIGS. 4A and 4B show that both EREG/AREG rabbit monoclonal antibodies are specific and recognize the unglycosylated form and the C-terminal fragment of the precursor proteins.

The assay performance of EREG/AREG IHC assays were evaluated on 8 colorectal cancer cases kindly provided by Dr. Paul Waring. Specimens were immunohistochemically stained for EREG expression with clone J5H1L1 and for AREG expression with J111H1L10 on a VENTANA BenchMark XT IHC/ISH instrument. The following instrument protocols were used:

TABLE 4

| EREG | AREG |
|---|---|
| 1. Paraffin [Selected]; | 1. Paraffin [Selected]; |
| 2. Deparaffinization [Selected]; | 2. Deparaffinization [Selected]; |
| 3. Cell Conditioning [Selected]; | 3. Cell Conditioning [Selected]; |
| 4. CC1 [Selected]; | 4. CC1 [Selected]; |
| 5. CC1 8 Min [Selected]; | 5. CC1 8 Min [Selected]; |
| 6. CC1 16 Min [Selected]; | 6. CC1 16 Min [Selected]; |
| 7. CC1 24 Min [Selected]; | 7. CC1 24 Min [Selected]; |
| 8. CC1 32 Min [Selected]; | 8. CC1 32 Min [Selected]; |
| 9. CC1 40 Min [Selected]; | 9. CC1 40 Min [Selected]; |
| 10. CC1 48 Min [Selected]; | 10. CC1 48 Min [Selected]; |
| 11. CC1 56 Min [Selected]; | 11. CC1 56 Min [Selected]; |
| 12. CC1 64 Min [Selected]; | 12. CC1 64 Min [Selected]; |
| 13. Primary Antibody [Selected]; | 13. Pre Primary Peroxidase Inhib. [Selected]; |
| 14. Primary Antibody Temperature [Selected]; | 14. Primary Antibody [Selected]; |
| 15. Warmup Slide to Ab Incubation Temperatures [Primary Antibody] | 15. Primary Antibody Temperature [Selected]; |
| 16. Apply Coverslip, One Drop of [ANTIBODY 3] (Antibody), and Incubate for [0 Hr 16 Min]; | 16. Warmup Slide to Ab Incubation Temperatures [Primary Antibody] |
| 17. Post Primary Peroxidase Inhib. [Selected]; | 17. Apply Coverslip, One Drop of [ANTIBODY 81] (Antibody), and Incubate for [0 Hr 12 Min]; |
| 18. Counterstain [Selected]; | 18. Counterstain [Selected]; |
| 19. Apply one drop of [HEMATOXYLIN II] (Counterstain), Apply Coverslip, and Incubate for [4 Minutes] | 19. Apply one drop of [HEMATOXYLIN II] (Counterstain), Apply Coverslip, and Incubate for [4 Minutes] |
| 20. Post Counterstain [Selected] | 20. Post Counterstain [Selected] |
| 21. Apply one drop of [BLUING REAGENT] (Post Counterstain), Apply Coverslip, and Incubate for [4 Minutes]. | 21. Apply one drop of [BLUING REAGENT] (Post Counterstain), Apply Coverslip, and Incubate for [4 Minutes]. |

The stained samples were scored by a trained pathologist. Both IHC detected heterogeneous EREG/AREG protein expression resulting in variable signal intensity and patterns of staining (Table 5).

TABLE 5

| | EREG IHC | | | AREG IHC | | |
|---|---|---|---|---|---|---|
| CASE ID | Staining Intensity (0-3) | % Positive | Comments | Staining Intensity (0-3) | % Positive | Comments |
| 08A-3404-E | 0 | 0 | | 0 | 0 | Cytoblush |
| 08A-822-C | 0 | 0 | | 2 (membrane) | <1 | Edge effect |
| 08A-498-D | 2 (membrane) | 50 | Cytoblush | 3 (punctate/granular) | | |
| 07A-10206-1B | 1 (cytoplasmic) | 10 | | 1 (cytoplasmic) | 45 | |
| | 3 (membrane) | | | 3 (membrane) | 35 | |
| 09A-3848-B | 2 (membrane) | 50 | | 3 (punctate/granular) | | |
| 07A-20580-F | 3 (membrane) | 10 | | 3 (membrane) | 50 | |
| 08A-1198-C | 3 (membrane) | 75 | | 3 (punctate/granular) | | |
| 06A-18241-C | 3 (membrane) | 40 | | 3 (membrane) | 10 | |

Figure 5A:
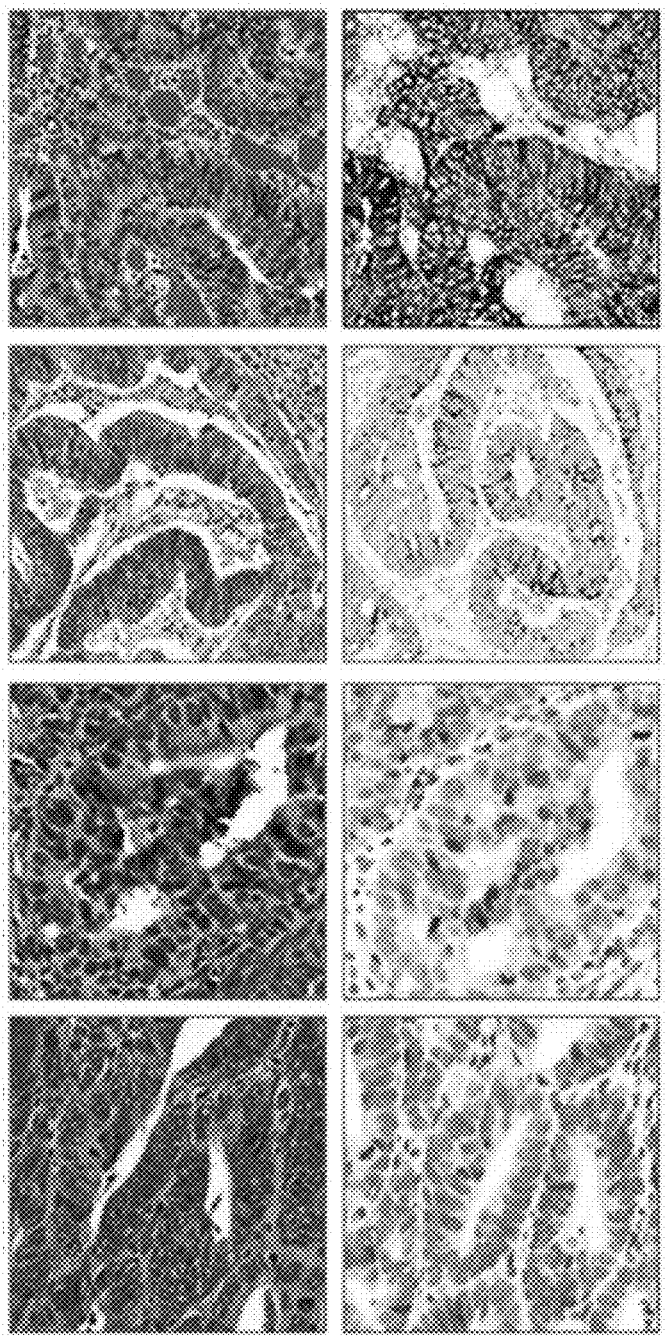
FIGS. 5A-5C provide representative images of IHC results for EREG and AREG IHC, demonstrating membrane, granular/punctate, and cytoplasmic staining.
Figure 5B:
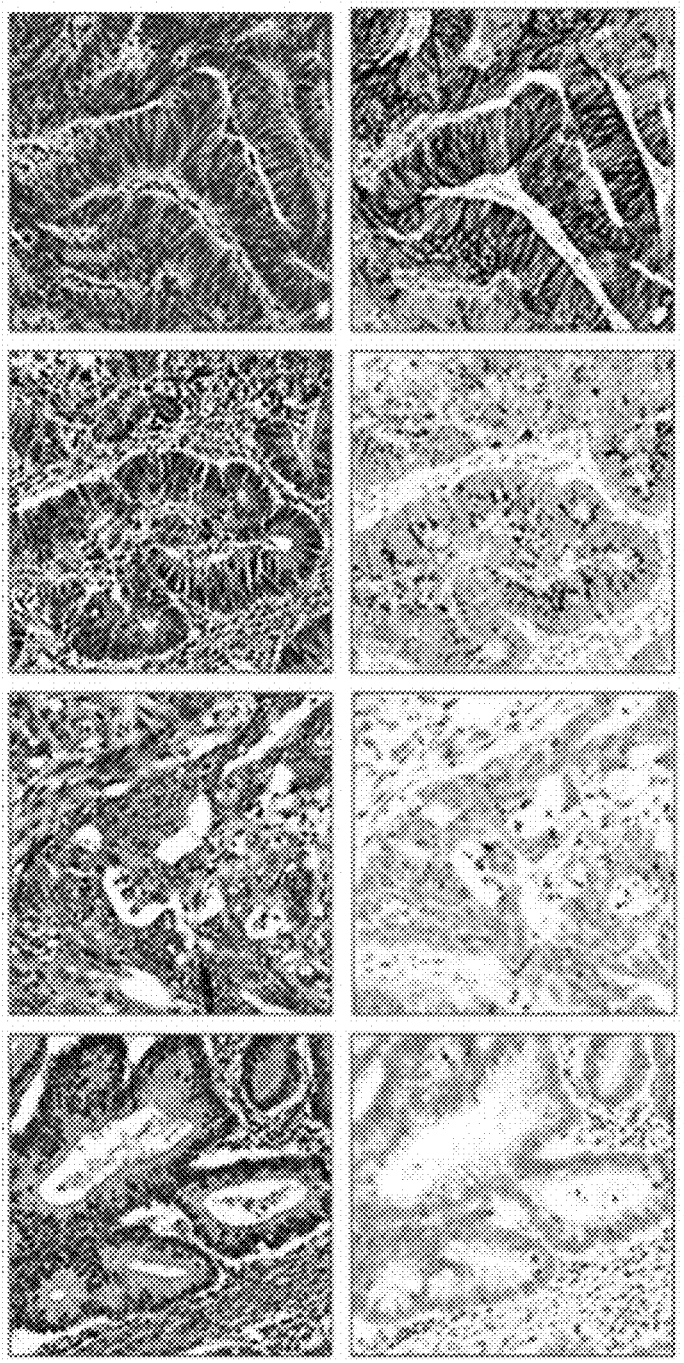
Figure 5C:
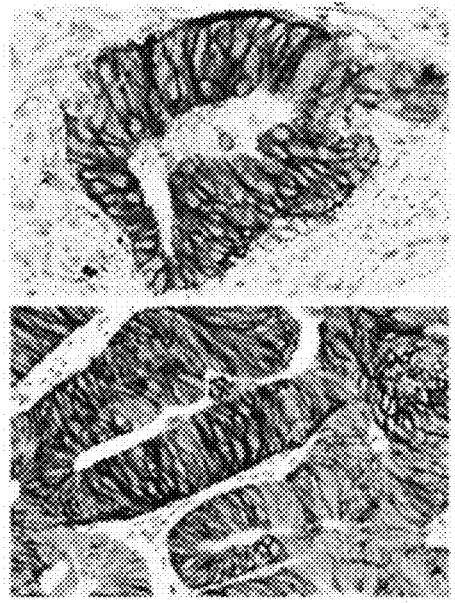
Figure 5C:
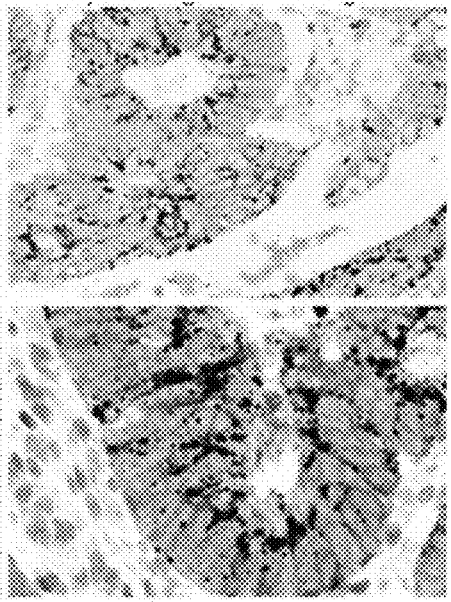

Three types of staining pattern were characteristic across 8 tissue samples: cytoplasmic, membranous and granular/punctate staining (FIG. 5A-5C). EREG/AREG cytoplasmic expression is likely due to the detection of the cytosolic fragments of the precursor proteins after their cleavage. Granular/punctate staining is associated with the detection of the ligands incorporated into exosomes. The membranous staining corresponds to the identification of the membrane anchored precursor EREG/AREG proteins.

Example 4. Generation of Anti-Human Pro-Epiregulin Antibodies Against Amino Acids 156-169 of SEQ ID NO: 1

Rabbit monoclonal antibodies were raised against synthetic peptides corresponding to the C-terminus of human precursor EREG proteins. As a result, these antibodies detect the membrane-bound forms of pro-EREG protein prior to their cleavage but also detect the cytosolic fragment of the precursor proteins prior to being transported to the cell membrane.

Anti-human pro-epiregulin rabbit monoclonal antibodies were generated as schematically depicted in FIG. 1. Briefly, the peptide fragment of amino acid residues 156-169 of SEQ ID NO: 1 (sequence YERVTSGDPELPQV, SEQ ID NO: 36) was synthesized and an additional two amino acids (Cys-Gly) were added to the N-terminus of the sequence during synthesis to facilitate conjugation to the carrier protein KLH, an extensively used carrier protein for stimulating a substantial immune response via antibody production. New Zealand White rabbits were immunized with KLH conjugated human pro-epiregulin antigen emulsified with complete Freund's adjuvant followed by a series of human pro-epiregulin antigen booster emulsified with incomplete Freund's adjuvant. The antibody-expressing cells were screened by enzyme-linked immunoabsorbant assay (ELISA) using the human pro-epiregulin antigen. All ELISA positive clones were further screened by immunohistochemistry (IHC), and the clone producing the antibody with the highest specificity was selected. For recombinant production of anti-human pro-epiregulin antibodies, cDNA coding for the heavy chain and light chain sequences of the antibodies were cloned, expressed by co-transfection, and screened for binding to human pro-epiregulin by IHC.

Anti-human pro-epiregulin monoclonal antibodies J89H12L3 and J89H12L8 were produced using these methods and subsequently purified by Protein A affinity chromatography. The heavy and light chain variable region sequences of the J89H12L3 antibody are as follows.

The amino acid sequence of the heavy chain variable region comprises the following:

```
                                        (SEQ ID NO: 33)
KSVEESGGRLVTPGTPLTLTCTVSGIDLSTFAMAWVRQAPGKGLEYIGFI

SLSDATYYATWAKGRFTISKSSSTTVDLKIITPTAEDTATYFCARVVGDS

SGYPNTFHPWGPGTLVTVSS
```

The amino acid sequence of the light chain variable region comprises the following:

```
                                        (SEQ ID NO: 34)
QVLTQTPSPVSAAVGGTVTINCQASQSIHNSDFLAWYQQKPGQPPKLLIY

RASKLPSGVPSRFKGSGSGTQFTLTISDLECDDAATYYCQGTYYSGGWYF

TFGGGTEVVVK.
```

The heavy and light chain variable region sequences of the J89H12L8 antibody are as follows.

The amino acid sequence of the heavy chain variable region comprises the following:

```
                                        (SEQ ID NO: 33)
KSVEESGGRLVTPGTPLTLTCTVSGIDLSTFAMAWVRQAPGKGLEYIGFI

SLSDATYYATWAKGRFTISKSSSTTVDLKIITPTAEDTATYFCARVVGDS

SGYPNTFHPWGPGTLVTVSS
```

The amino acid sequence of the light chain variable region comprises the following:

```
                                        (SEQ ID NO: 35)
QVLTQTPSPVSAAVGGTVTINCQASQNIHNSDFLAWYQQKPGQPPKLLIY

RASKLPSGVPSRFKGSGSGTQFTLTISDLECDDAATYYCQGTYYSGGWYF

TFGGGTEVVVK.
```

Figure 6:
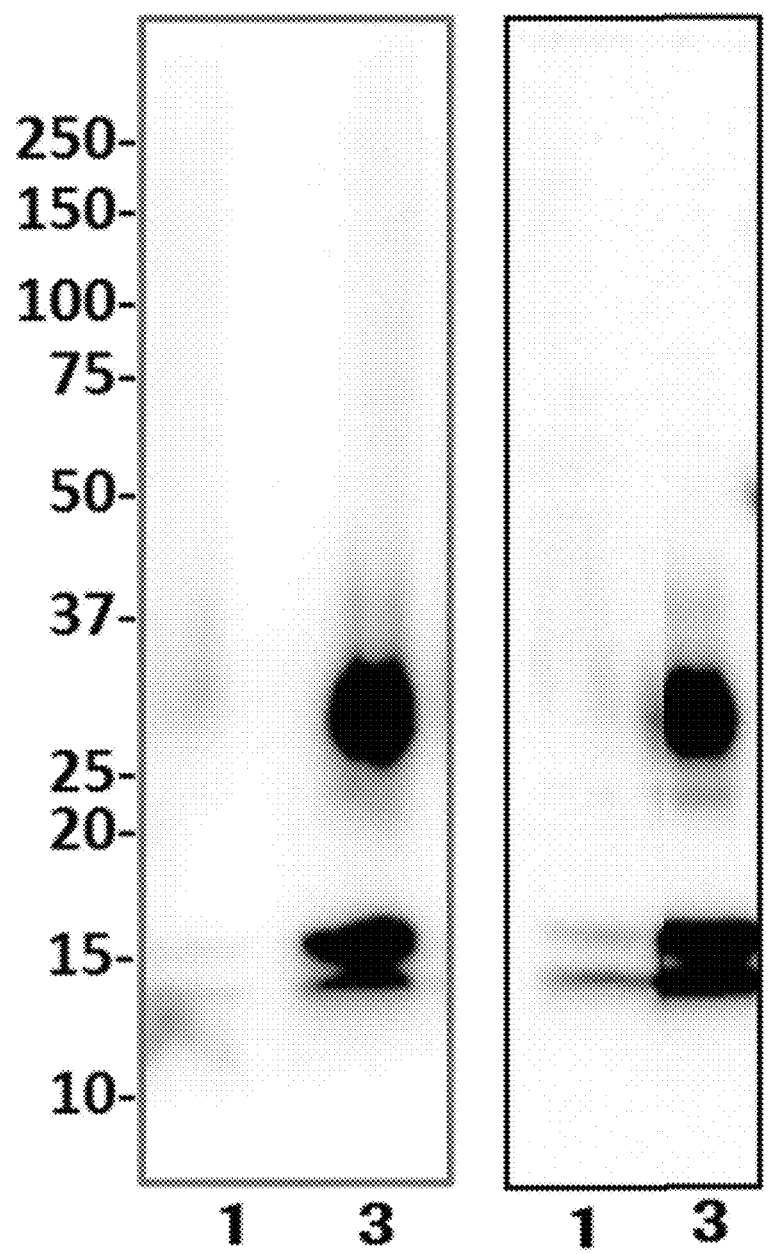
FIG. 6 is a picture of a Western blot (WB) analysis comparting EREG antibody clone J89H12L3 with clone D405I.

The obtained antibodies were tested via Western blot for specificity. Antibody clone D4O5I (Cell Signaling Technologies, Inc.) was used as a positive control. In brief, 10 total protein was loaded and separated on 4-20% SDS-PAGE gel followed by transferring to PVDF membrane. The membrane was then blocked in TBST with 5% BSA followed by incubation with 0.2 ug/ml of J89H12L3 and 0.4 ug/ml of D4O5I. Pro epiregulin and its propeptide were detected by goat anti rabbit-HRP conjugate and visualized by SuperSignal™ West Pico Chemiluminescent Substrate (Thermo-Fisher Scientific 34079). FIG. 6 demonstrates such a Western blot for clone J89H12L3. The western blot was negative in negative control A549 cell line (lane 1) for both clones. Glycosylated (30 kDa) and unglycosylated (17 and 18 kDa) pro-EREG were detected with both clones in cell lysates from HCC827 (right lane) cells.

The obtained antibodies were also tested in an IHC analysis in xenograft and primary tissue. The IHC was processed with automatic staining system (BenchMark ULTRA, Roche) using the following protocol. FFPE tissue sections were deparaffinized and heated in EDTA antigen retrieval buffer for 64 min before the rabbit anti-human EREG monoclonal antibodies were added to the tissue sections. The incubation time for the rabbit primary antibody was 16 min at 37° C., and it was followed with a standard OptiView detection protocol from Roche.

Figure 7:
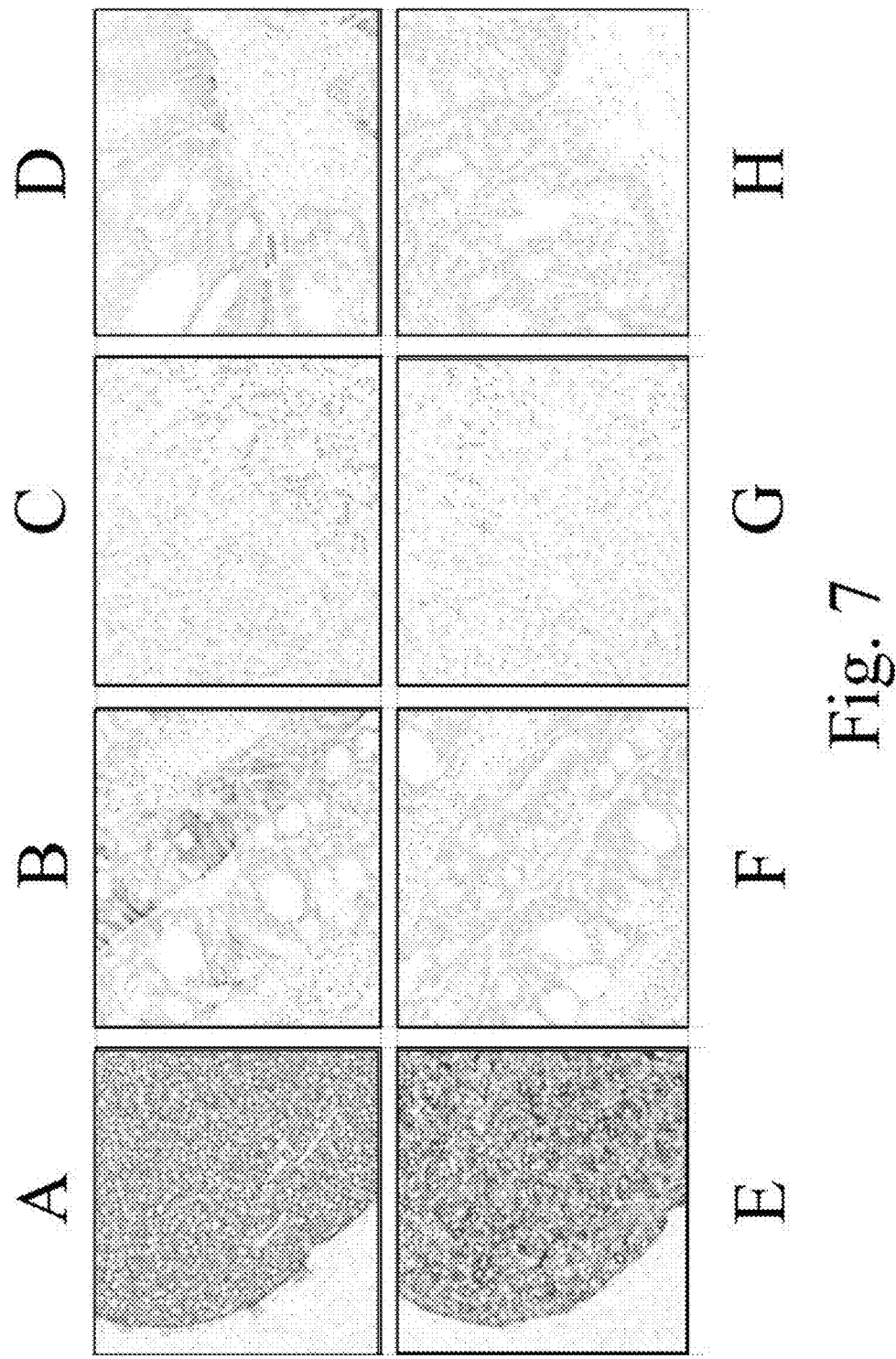
FIG. 7 demonstrates images of IHC analysis of EREG protein expression in xenograft. Samples A-D are stained with clone J89H12L3. Samples E-G are stained with clone D405I. Samples A and E are xenografts from SKE23 cells. Samples B and F are xenografts from PLR124EREG+/− cells. Samples C and G are xenografts from SK-Hep1 cells. Samples D and H are xenografts from PLR124EREG −/− cells. Brown indicates positive staining.

FIG. 7 is a comparison between J89H12L3 and D4O5I in various xenografts. Staining is strong in highest EREG expressor—SKE23 cells (A), weak in PLR124EREG+/− cells (B), negative in SK-Hep1 cells (C), and weak in PLR124EREG −/− cells (D) using clone J89H12L3. Similarly clone D4O5I stained SKE23 cells (E) strongly, but it is very weak in PLR124EREG+/− cells (F) and negative for both SK-Hep1 (G) and PLR124EREG −/− cells (H).

Figure 8:
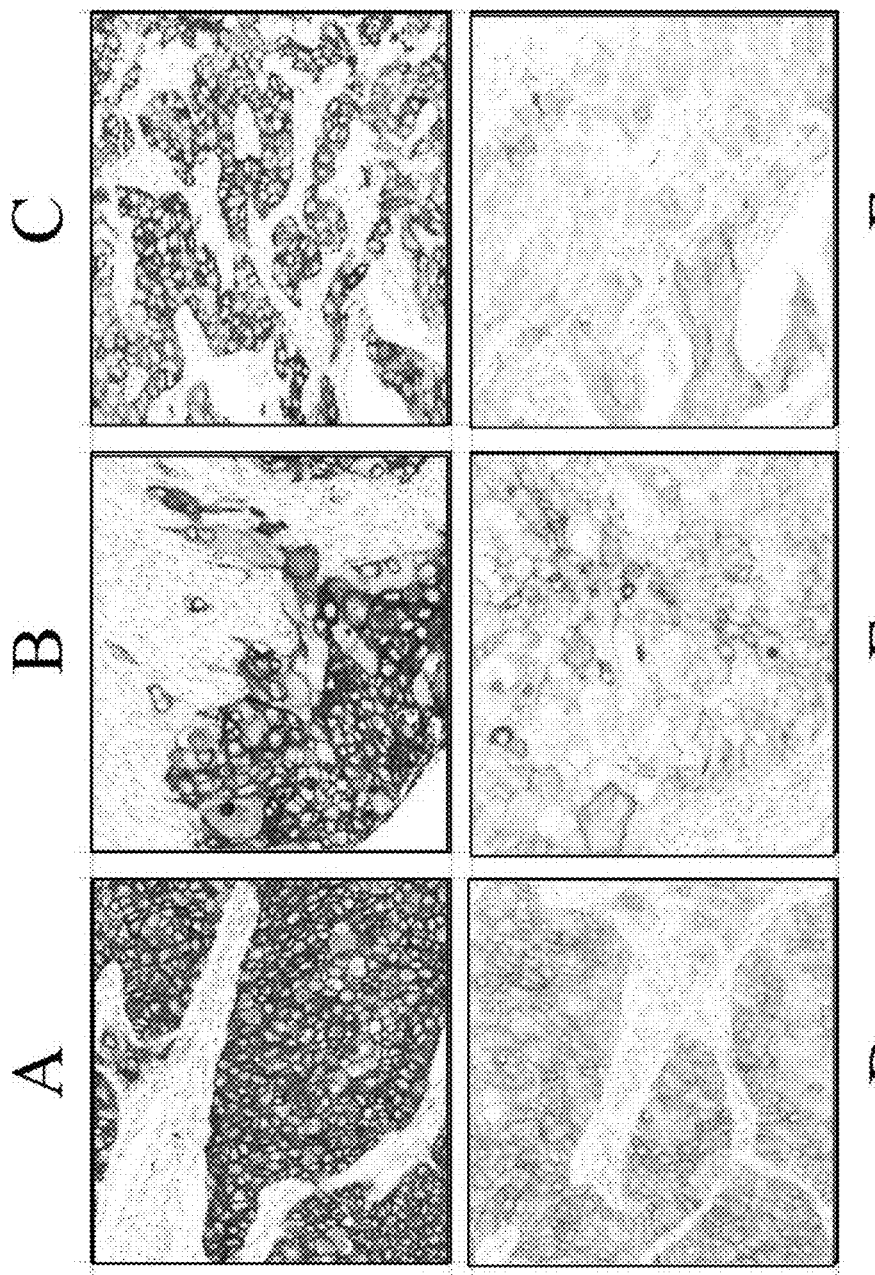
FIG. 8 is a comparison between J89H12L3 and D405I in lung squamous cell carcinoma (SCC) tissue. Images A-C are tissues stained with clone J89H12L3. Images D-F are tissues stained with clone D405I.

FIG. 8 is a comparison between J89H12L3 and D4O5I in lung squamous cell carcinoma (SCC) tissue. Higher intensity is seen in cancer tissues stained with clones J89H12L3 (A-C) when compared to those tissues stained with clone D4O5I (Cell Signaling Technologies, Inc., Danvers, Mass.) (D-F).

Figure 9:
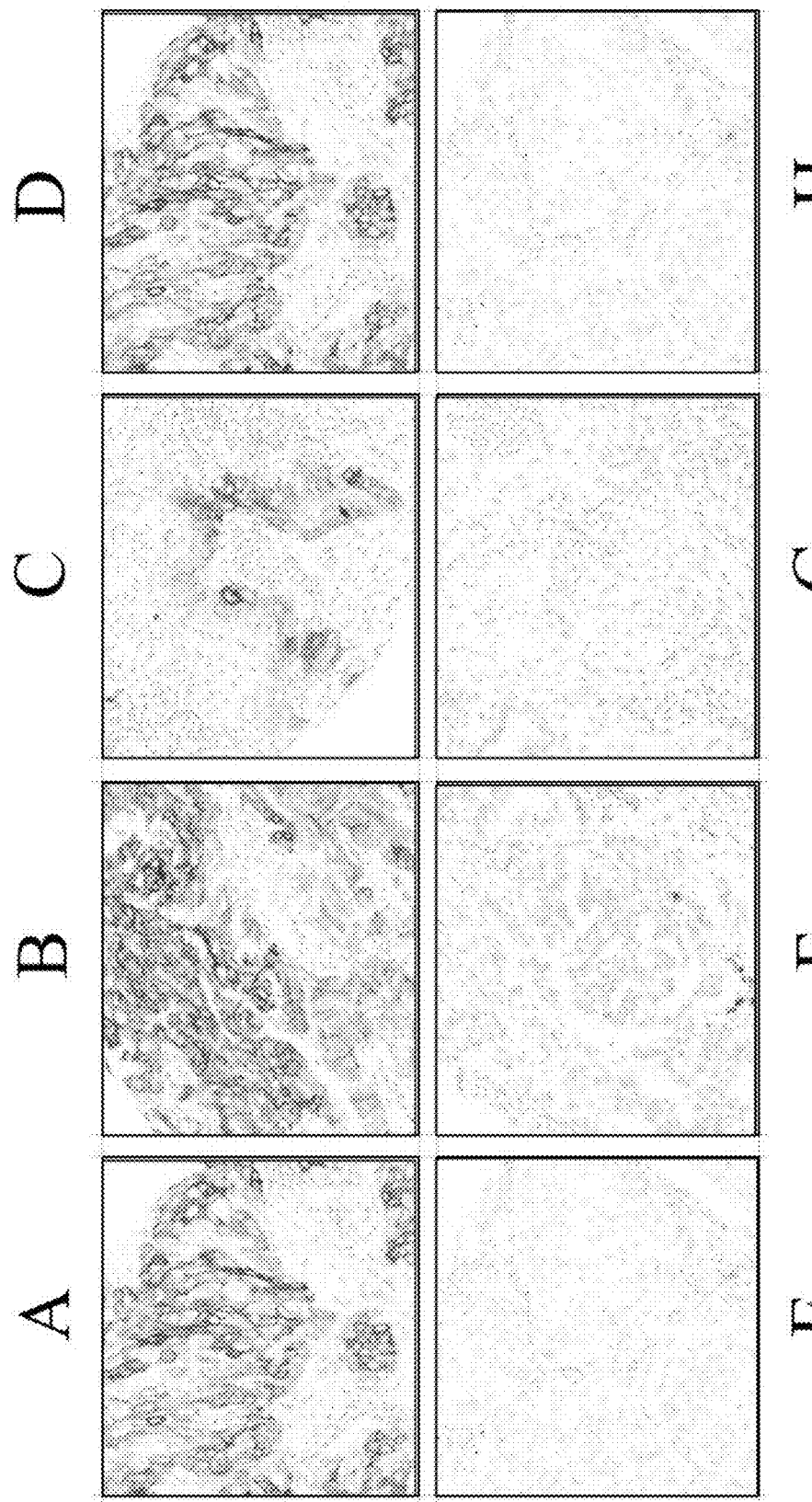
FIG. 9 is a comparison between J89H12L3 and D405I in lung adenocarcinoma and adenosquamous cell carcinoma. Images A-D are tissues stained with clone J89H12L3. Images E-H are tissues stained with clone D405I.

FIG. 9 is a comparison between J89H12L3 and D4O5I in lung adenocarcinoma and adenosquamous cell carcinoma. Higher intensity is seen in cancer tissues stained with clones J89H12L3 (A-D) when compared to those tissues stained with clone D4O5I (E-H).

Figure 10:
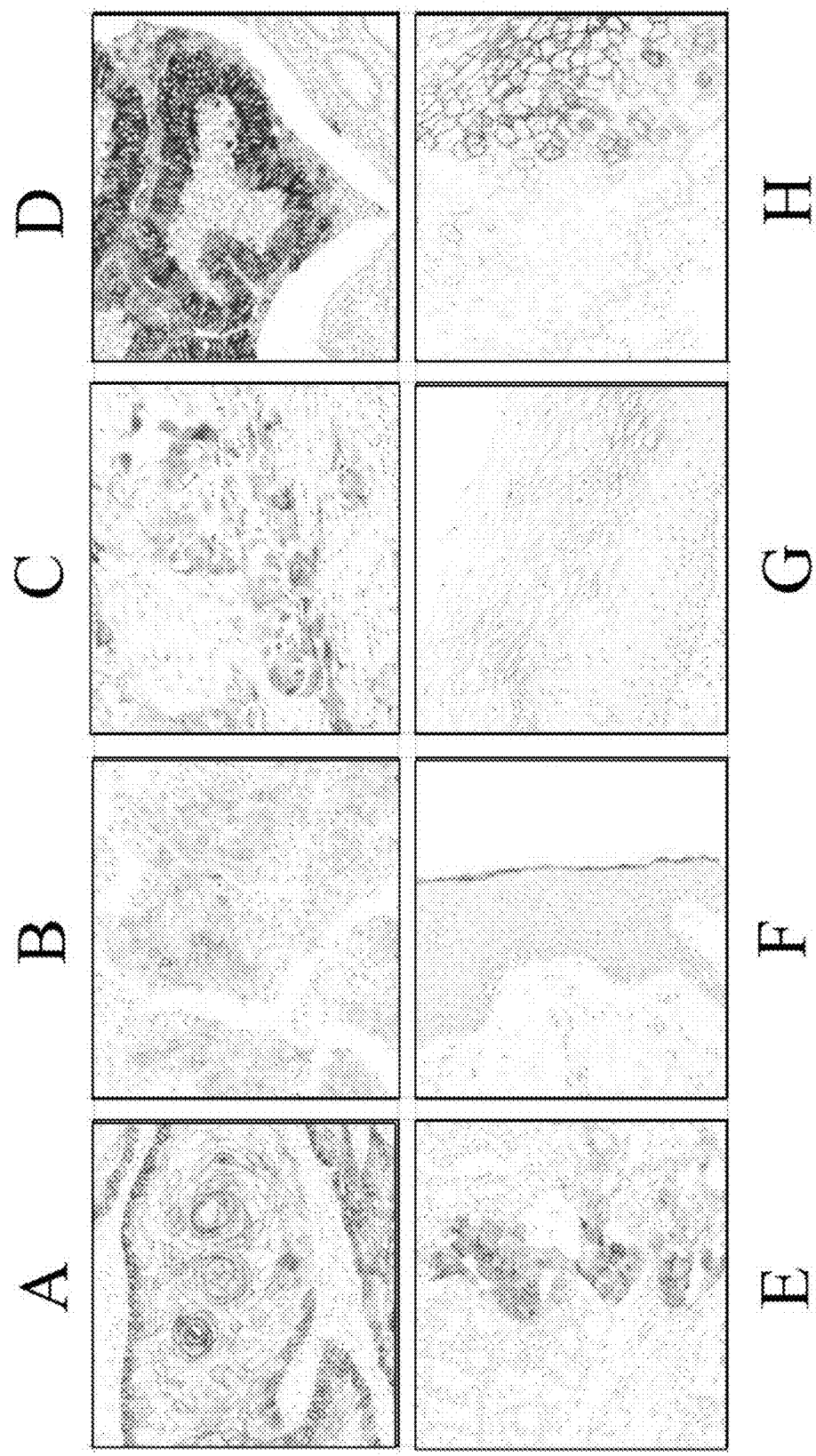
FIG. 10 is an IHC analysis of EREG protein expression in normal and tumor tissues using clone J89H12L3. Images are of tissues stained with J89H12L3 as follows: skin squamous cell carcinoma (A), hepatocellular carcinoma (B), bladder transitional cell carcinoma (C), colon adenocarcinoma (D), lung adenocarcinoma (E), skin (F), cervix (G), and esophagus (H).

FIG. 10 is an IHC analysis of EREG protein expression in normal and tumor tissues using clone J89H12L3. Moderate to strong staining is seen in skin squamous cell carcinoma (A), hepatocellular carcinoma (B), bladder transitional cell carcinoma (C), colon adenocarcinoma (D), lung adenocarcinoma (E), skin (F), cervix (G), and esophagus (H).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antibody or antibody fragment capable of specifically binding to amino acids 238-252 of SEQ ID NO: 36, wherein said antibody comprises:
   a heavy chain variable domain (VH) amino acid sequence comprising the following heavy chain hypervariable regions (HVR-Hs):
   (a) an HVR-H1 comprising SEQ ID NO: 37;
   (b) an HVR-H2 comprising SEQ ID NO: 38; and
   (c) an HVR-H3 comprising SEQ ID NO: 39; and
   a light chain variable domain (VL) amino acid sequence comprising the following light chain hypervariable regions (HVR-Ls):
   (d) an HVR-L1 comprising SEQ ID NO: 44;
   (e) an HVR-L2 comprising SEQ ID NO: 45; and
   (f) an HVR-L3 comprising SEQ ID NO: 46.

2. The antibody or antibody fragment of claim 1, wherein the VH amino acid sequence further comprises the following variable domain framework regions (FRs):
   (g) FR-H1 comprising SEQ ID NO: 40;
   (h) FR-H2 comprising SEQ ID NO: 41;
   (i) FR-H3 comprising SEQ ID NO: 42; and
   (j) FR-H4 comprising SEQ ID NO: 43.

3. The antibody or antibody fragment of claim 1, wherein the VL amino acid sequence further comprises the following variable domain framework regions (FRs):
   (k) FR-L1 comprising SEQ ID NO: 47;
   (l) FR-L2 comprising SEQ ID NO: 48;
   (m) FR-L3 comprising SEQ ID NO: 49; and
   (n) FR-L4 comprising SEQ ID NO: 50.

4. The antibody or antibody fragment of claim 1, wherein the VH amino acid sequence has at least 95% sequence identity to SEQ ID NO: 51.

5. The antibody or antibody fragment of claim 4, wherein the VH amino acid sequence comprises SEQ ID NO: 51.

6. The antibody or antibody fragment of claim 4, wherein the VL amino acid sequence comprises SEQ ID NO: 52.

7. The antibody or antibody fragment of claim 4, wherein the VH amino acid sequence comprises SEQ ID NO: 51 and the VL amino acid sequence comprises SEQ ID NO: 52.

8. The antibody of claim 1, wherein the antibody is a monoclonal antibody.

9. The antibody of claim 8, wherein the monoclonal antibody is a rabbit monoclonal antibody.

10. The antibody of claim 8, wherein the monoclonal antibody is an IgG antibody.

11. The antibody fragment of claim 1, wherein the antibody fragment is selected from the group consisting of Fab, single chain variable fragment (scFv), Fv, Fab', Fab'-SH, F(ab')2, and diabody.

12. The antibody or antibody fragment of claim 1, wherein the VL amino acid sequence has at least 95% sequence identity to SEQ ID NO: 52.

13. The antibody or antibody fragment of claim 1, wherein the VH amino acid sequence has at least 95% sequence identity to SEQ ID NO: 51, and the VL amino acid sequence has at least 95% sequence identity to SEQ ID NO: 52.

14. A method of detecting the presence or expression level of human amphiregulin in a biological sample comprising:
   contacting the biological sample with the antibody or antibody fragment of claim 1; and
   detecting the presence of the bound antibody or antibody fragment.

15. The method of claim 14, wherein the detecting is by immunohistochemistry, immunofluorescence, or immunoblot.

16. The method of claim 14, wherein the biological sample comprises a fixed tissue.

17. The method of claim 16, wherein the fixed tissue is a formalin-fixed paraffin embedded (FFPE) tissue.

18. The method of claim 14, wherein the biological sample is from a subject having or predisposed to cancer.

19. The method of claim 18, wherein the cancer is colon cancer, breast cancer, or lung cancer.

* * * * *

SEQUENCE LISTING

```
<160> NUMBER OF SEQ ID NOS: 52

<210> SEQ ID NO 1
<211> LENGTH: 169
<212> TYPE: PRT
<213> ORGANISM: Homo sapiens

<400> SEQUENCE: 1

Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
        35                  40                  45

Thr Ala Leu Val Gln Thr Glu Asp Asn Pro Arg Val Ala Gln Val Ser
    50                  55                  60

Ile Thr Lys Cys Ser Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
                85                  90                  95

Gly Tyr Thr Gly Val Arg Cys Glu His Phe Phe Leu Thr Val His Gln
            100                 105                 110

Pro Leu Ser Lys Glu Tyr Val Ala Leu Thr Val Ile Leu Ile Ile Leu
        115                 120                 125

Phe Leu Ile Thr Val Val Gly Ser Thr Tyr Tyr Phe Cys Arg Trp Tyr
    130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
```

```
                        165
```

<210> SEQ ID NO 2
<211> LENGTH: 5
<212> TYPE: PRT
<213> ORGANISM: Oryctolagus cuniculus

<400> SEQUENCE: 2

Arg Tyr Gly Met Ser
1               5

<210> SEQ ID NO 3
<211> LENGTH: 16
<212> TYPE: PRT
<213> ORGANISM: Oryctolagus cuniculus

<400> SEQUENCE: 3

Ser Ile Asn Arg Thr Ala Tyr Thr Tyr Tyr Ala Thr Trp Ala Lys Gly
1               5                   10                  15

<210> SEQ ID NO 4
<211> LENGTH: 15
<212> TYPE: PRT
<213> ORGANISM: Oryctolagus cuniculus

<400> SEQUENCE: 4

Gly Leu Thr Tyr Gly Gly Ser Asp Tyr Asp Tyr Asp Asp Ala Leu
1               5                   10                  15

<210> SEQ ID NO 5
<211> LENGTH: 29
<212> TYPE: PRT
<213> ORGANISM: Oryctolagus cuniculus

<400> SEQUENCE: 5

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 6
<211> LENGTH: 14
<212> TYPE: PRT
<213> ORGANISM: Oryctolagus cuniculus

<400> SEQUENCE: 6

Trp Val Arg Gln Ala Pro Gly Lys Gly Leu Glu Tyr Ile Gly
1               5                   10

<210> SEQ ID NO 7
<211> LENGTH: 30
<212> TYPE: PRT
<213> ORGANISM: Oryctolagus cuniculus

<400> SEQUENCE: 7

Arg Phe Thr Ile Ser Arg Thr Ser Thr Thr Val Asp Leu Arg Met Thr
1               5                   10                  15

Ser Leu Thr Thr Glu Asp Thr Ala Thr Tyr Phe Cys Ala Arg
            20                  25                  30

<210> SEQ ID NO 8
<211> LENGTH: 11
<212> TYPE: PRT
<213> ORGANISM: Oryctolagus cuniculus

<400> SEQUENCE: 8

Trp Gly Pro Gly Thr Leu Val Thr Val Ser Ser
1               5                   10

<210> SEQ ID NO 9
<211> LENGTH: 13
<212> TYPE: PRT
<213> ORGANISM: Oryctolagus cuniculus

<400> SEQUENCE: 9

Gln Ala Ser Gln Ser Val Tyr Lys Asn Lys Asn Leu Ala
1               5                   10

<210> SEQ ID NO 10
<211> LENGTH: 7
<212> TYPE: PRT
<213> ORGANISM: Oryctolagus cuniculus

<400> SEQUENCE: 10

Arg Ala Ser Thr Leu Ala Ser
1               5

<210> SEQ ID NO 11
<211> LENGTH: 13
<212> TYPE: PRT
<213> ORGANISM: Oryctolagus cuniculus

<400> SEQUENCE: 11

Gln Gly Glu Phe Ser Cys Ser Thr Phe Asp Cys Ile Leu
1               5                   10

<210> SEQ ID NO 12
<211> LENGTH: 22
<212> TYPE: PRT
<213> ORGANISM: Oryctolagus cuniculus

<400> SEQUENCE: 12

Gln Val Leu Thr Gln Thr Pro Ser Ser Val Ser Ala Ala Val Gly Gly
1               5                   10                  15

Thr Val Thr Ile Asn Cys
            20

<210> SEQ ID NO 13
<211> LENGTH: 15
<212> TYPE: PRT
<213> ORGANISM: Oryctolagus cuniculus

<400> SEQUENCE: 13

Trp Tyr Gln Gln Lys Pro Gly Gln Pro Pro Lys Leu Leu Ile Tyr
1               5                   10                  15

<210> SEQ ID NO 14
<211> LENGTH: 32
<212> TYPE: PRT
<213> ORGANISM: Oryctolagus cuniculus

<400> SEQUENCE: 14

Gly Val Ser Ser Arg Phe Lys Gly Ser Gly Ser Gly Thr Gln Phe Thr
1               5                   10                  15

Leu Thr Ile Ser Gly Val Gln Cys Ala Asp Ala Ala Thr Tyr Tyr Cys
            20                  25                  30

```
<210> SEQ ID NO 15
<211> LENGTH: 10
<212> TYPE: PRT
<213> ORGANISM: Oryctolagus cuniculus

<400> SEQUENCE: 15

Phe Gly Gly Gly Thr Glu Met Val Val Lys
1               5                   10

<210> SEQ ID NO 16
<211> LENGTH: 120
<212> TYPE: PRT
<213> ORGANISM: Oryctolagus cuniculus

<400> SEQUENCE: 16

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Tyr Gly
                20                  25                  30

Met Ser Trp Val Arg Gln Ala Pro Gly Lys Gly Leu Glu Tyr Ile Gly
            35                  40                  45

Ser Ile Asn Arg Thr Ala Tyr Thr Tyr Tyr Ala Thr Trp Ala Lys Gly
        50                  55                  60

Arg Phe Thr Ile Ser Arg Thr Ser Thr Thr Val Asp Leu Arg Met Thr
65                  70                  75                  80

Ser Leu Thr Thr Glu Asp Thr Ala Thr Tyr Phe Cys Ala Arg Gly Leu
                85                  90                  95

Thr Tyr Gly Gly Ser Asp Tyr Asp Tyr Asp Asp Ala Leu Trp Gly Pro
            100                 105                 110

Gly Thr Leu Val Thr Val Ser Ser
        115                 120

<210> SEQ ID NO 17
<211> LENGTH: 112
<212> TYPE: PRT
<213> ORGANISM: Oryctolagus cuniculus

<400> SEQUENCE: 17

Gln Val Leu Thr Gln Thr Pro Ser Ser Val Ser Ala Ala Val Gly Gly
1               5                   10                  15

Thr Val Thr Ile Asn Cys Gln Ala Ser Gln Ser Val Tyr Lys Asn Lys
                20                  25                  30

Asn Leu Ala Trp Tyr Gln Gln Lys Pro Gly Gln Pro Pro Lys Leu Leu
            35                  40                  45

Ile Tyr Arg Ala Ser Thr Leu Ala Ser Gly Val Ser Ser Arg Phe Lys
        50                  55                  60

Gly Ser Gly Ser Gly Thr Gln Phe Thr Leu Thr Ile Ser Gly Val Gln
65                  70                  75                  80

Cys Ala Asp Ala Ala Thr Tyr Tyr Cys Gln Gly Glu Phe Ser Cys Ser
                85                  90                  95

Thr Phe Asp Cys Ile Leu Phe Gly Gly Gly Thr Glu Met Val Val Lys
            100                 105                 110

<210> SEQ ID NO 18
<211> LENGTH: 5
<212> TYPE: PRT
<213> ORGANISM: Oryctolagus cuniculus

<400> SEQUENCE: 18
```

Thr Phe Ala Met Ala
1               5

<210> SEQ ID NO 19
<211> LENGTH: 16
<212> TYPE: PRT
<213> ORGANISM: Oryctolagus cuniculus

<400> SEQUENCE: 19

Phe Ile Ser Leu Ser Asp Ala Thr Tyr Tyr Ala Thr Trp Ala Lys Gly
1               5                   10                  15

<210> SEQ ID NO 20
<211> LENGTH: 14
<212> TYPE: PRT
<213> ORGANISM: Oryctolagus cuniculus

<400> SEQUENCE: 20

Val Val Gly Asp Ser Ser Gly Tyr Pro Asn Thr Phe His Pro
1               5                   10

<210> SEQ ID NO 21
<211> LENGTH: 29
<212> TYPE: PRT
<213> ORGANISM: Oryctolagus cuniculus

<400> SEQUENCE: 21

Lys Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser
            20                  25

<210> SEQ ID NO 22
<211> LENGTH: 14
<212> TYPE: PRT
<213> ORGANISM: Oryctolagus cuniculus

<400> SEQUENCE: 22

Trp Val Arg Gln Ala Pro Gly Lys Gly Leu Glu Tyr Ile Gly
1               5                   10

<210> SEQ ID NO 23
<211> LENGTH: 31
<212> TYPE: PRT
<213> ORGANISM: Oryctolagus cuniculus

<400> SEQUENCE: 23

Arg Phe Thr Ile Ser Lys Ser Ser Thr Thr Val Asp Leu Lys Ile
1               5                   10                  15

Ile Thr Pro Thr Ala Glu Asp Thr Ala Thr Tyr Phe Cys Ala Arg
            20                  25                  30

<210> SEQ ID NO 24
<211> LENGTH: 11
<212> TYPE: PRT
<213> ORGANISM: Oryctolagus cuniculus

<400> SEQUENCE: 24

Trp Gly Pro Gly Thr Leu Val Thr Val Ser Ser
1               5                   10

<210> SEQ ID NO 25
<211> LENGTH: 13
<212> TYPE: PRT

<213> ORGANISM: Oryctolagus cuniculus

<400> SEQUENCE: 25

Gln Ala Ser Gln Ser Ile His Asn Ser Asp Phe Leu Ala
1               5                   10

<210> SEQ ID NO 26
<211> LENGTH: 13
<212> TYPE: PRT
<213> ORGANISM: Oryctolagus cuniculus

<400> SEQUENCE: 26

Gln Ala Ser Gln Asn Ile His Asn Ser Asp Phe Leu Ala
1               5                   10

<210> SEQ ID NO 27
<211> LENGTH: 7
<212> TYPE: PRT
<213> ORGANISM: Oryctolagus cuniculus

<400> SEQUENCE: 27

Arg Ala Ser Lys Leu Pro Ser
1               5

<210> SEQ ID NO 28
<211> LENGTH: 12
<212> TYPE: PRT
<213> ORGANISM: Oryctolagus cuniculus

<400> SEQUENCE: 28

Gln Gly Thr Tyr Tyr Ser Gly Gly Trp Tyr Phe Thr
1               5                   10

<210> SEQ ID NO 29
<211> LENGTH: 22
<212> TYPE: PRT
<213> ORGANISM: Oryctolagus cuniculus

<400> SEQUENCE: 29

Gln Val Leu Thr Gln Thr Pro Ser Pro Val Ser Ala Ala Val Gly Gly
1               5                   10                  15

Thr Val Thr Ile Asn Cys
            20

<210> SEQ ID NO 30
<211> LENGTH: 15
<212> TYPE: PRT
<213> ORGANISM: Oryctolagus cuniculus

<400> SEQUENCE: 30

Trp Tyr Gln Gln Lys Pro Gly Gln Pro Pro Lys Leu Leu Ile Tyr
1               5                   10                  15

<210> SEQ ID NO 31
<211> LENGTH: 32
<212> TYPE: PRT
<213> ORGANISM: Oryctolagus cuniculus

<400> SEQUENCE: 31

Gly Val Pro Ser Arg Phe Lys Gly Ser Gly Ser Gly Thr Gln Phe Thr
1               5                   10                  15

Leu Thr Ile Ser Asp Leu Glu Cys Asp Asp Ala Ala Thr Tyr Tyr Cys
            20                  25                  30

<210> SEQ ID NO 32
<211> LENGTH: 10
<212> TYPE: PRT
<213> ORGANISM: Oryctolagus cuniculus

<400> SEQUENCE: 32

Phe Gly Gly Gly Thr Glu Val Val Val Lys
1               5                   10

<210> SEQ ID NO 33
<211> LENGTH: 120
<212> TYPE: PRT
<213> ORGANISM: Oryctolagus cuniculus

<400> SEQUENCE: 33

Lys Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Phe Ala
            20                  25                  30

Met Ala Trp Val Arg Gln Ala Pro Gly Lys Gly Leu Glu Tyr Ile Gly
        35                  40                  45

Phe Ile Ser Leu Ser Asp Ala Thr Tyr Tyr Ala Thr Trp Ala Lys Gly
    50                  55                  60

Arg Phe Thr Ile Ser Lys Ser Ser Thr Thr Val Asp Leu Lys Ile
65                  70                  75                  80

Ile Thr Pro Thr Ala Glu Asp Thr Ala Thr Tyr Phe Cys Ala Arg Val
                85                  90                  95

Val Gly Asp Ser Ser Gly Tyr Pro Asn Thr Phe His Pro Trp Gly Pro
            100                 105                 110

Gly Thr Leu Val Thr Val Ser Ser
        115                 120

<210> SEQ ID NO 34
<211> LENGTH: 111
<212> TYPE: PRT
<213> ORGANISM: Oryctolagus cuniculus

<400> SEQUENCE: 34

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Ile His Asn Ser Asp
            20                  25                  30

Phe Leu Ala Trp Tyr Gln Gln Lys Pro Gly Gln Pro Pro Lys Leu Leu
        35                  40                  45

Ile Tyr Arg Ala Ser Lys Leu Pro Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Gln Gly Thr Tyr Tyr Ser Gly
                85                  90                  95

Gly Trp Tyr Phe Thr Phe Gly Gly Gly Thr Glu Val Val Val Lys
            100                 105                 110

<210> SEQ ID NO 35
<211> LENGTH: 111
<212> TYPE: PRT
<213> ORGANISM: Oryctolagus cuniculus

<400> SEQUENCE: 35

Gln Val Leu Thr Gln Thr Pro Ser Pro Val Ala Ala Val Gly Gly
1               5                   10                  15

Thr Val Thr Ile Asn Cys Gln Ala Ser Gln Asn Ile His Asn Ser Asp
            20                  25                  30

Phe Leu Ala Trp Tyr Gln Gln Lys Pro Gly Gln Pro Pro Lys Leu Leu
        35                  40                  45

Ile Tyr Arg Ala Ser Lys Leu Pro Ser Gly Val Pro Ser Arg Phe Lys
50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Gln Gly Thr Tyr Tyr Ser Gly
                85                  90                  95

Gly Trp Tyr Phe Thr Phe Gly Gly Gly Thr Glu Val Val Val Lys
            100                 105                 110

<210> SEQ ID NO 36
<211> LENGTH: 252
<212> TYPE: PRT
<213> ORGANISM: Homo sapiens

<400> SEQUENCE: 36

Met Arg Ala Pro Leu Pro Pro Ala Pro Val Val Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
50                  55                  60

Pro Val Ser Glu Met Pro Ser Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
            245                 250

-continued

```
<210> SEQ ID NO 37
<211> LENGTH: 5
<212> TYPE: PRT
<213> ORGANISM: Oryctolagus cuniculus

<400> SEQUENCE: 37

Ser Tyr Ala Ile Ser
1               5

<210> SEQ ID NO 38
<211> LENGTH: 17
<212> TYPE: PRT
<213> ORGANISM: Oryctolagus cuniculus

<400> SEQUENCE: 38

Phe Ile Val Gly Ser Ser Gly Ser Ala Tyr Tyr Ala Ser Trp Ala Lys
1               5                   10                  15

Ser

<210> SEQ ID NO 39
<211> LENGTH: 8
<212> TYPE: PRT
<213> ORGANISM: Oryctolagus cuniculus

<400> SEQUENCE: 39

Gly Leu Tyr Ser Gly Gly Asn Tyr
1               5

<210> SEQ ID NO 40
<211> LENGTH: 29
<212> TYPE: PRT
<213> ORGANISM: Oryctolagus cuniculus

<400> SEQUENCE: 40

Gln Ser Leu Glu Glu Ser Arg Gly Gly Leu Ile Lys Pro Gly Gly Thr
1               5                   10                  15

Leu Thr Leu Thr Cys Thr Val Ser Gly Phe Ser Leu Ser
            20                  25

<210> SEQ ID NO 41
<211> LENGTH: 14
<212> TYPE: PRT
<213> ORGANISM: Oryctolagus cuniculus

<400> SEQUENCE: 41

Trp Val Arg Gln Ala Pro Gly Asn Gly Leu Glu Trp Ile Gly
1               5                   10

<210> SEQ ID NO 42
<211> LENGTH: 32
<212> TYPE: PRT
<213> ORGANISM: Oryctolagus cuniculus

<400> SEQUENCE: 42

Arg Ser Thr Ile Thr Arg Asp Thr Asn Leu Asn Thr Val Thr Leu Lys
1               5                   10                  15

Met Thr Ser Leu Thr Ala Ala Asp Thr Ala Thr Tyr Phe Cys Ala Lys
            20                  25                  30

<210> SEQ ID NO 43
<211> LENGTH: 11
<212> TYPE: PRT
<213> ORGANISM: Oryctolagus cuniculus
```

```
<400> SEQUENCE: 43

Trp Gly Pro Gly Thr Leu Val Thr Val Ser Ser
1               5                   10

<210> SEQ ID NO 44
<211> LENGTH: 13
<212> TYPE: PRT
<213> ORGANISM: Oryctolagus cuniculus

<400> SEQUENCE: 44

Gln Ser Ser Gln Ser Val Asp Glu Asn Asn Tyr Leu Ser
1               5                   10

<210> SEQ ID NO 45
<211> LENGTH: 7
<212> TYPE: PRT
<213> ORGANISM: Oryctolagus cuniculus

<400> SEQUENCE: 45

Arg Ala Ser Thr Leu Glu Ser
1               5

<210> SEQ ID NO 46
<211> LENGTH: 11
<212> TYPE: PRT
<213> ORGANISM: Oryctolagus cuniculus

<400> SEQUENCE: 46

Leu Gly Gly Tyr Ser Gly Tyr Ser Asp Asp Gly
1               5                   10

<210> SEQ ID NO 47
<211> LENGTH: 22
<212> TYPE: PRT
<213> ORGANISM: Oryctolagus cuniculus

<400> SEQUENCE: 47

Ala Val Leu Thr Gln Thr Pro Ser Pro Val Ser Ala Ala Val Gly Gly
1               5                   10                  15

Thr Val Ser Ile Ser Cys
            20

<210> SEQ ID NO 48
<211> LENGTH: 15
<212> TYPE: PRT
<213> ORGANISM: Oryctolagus cuniculus

<400> SEQUENCE: 48

Trp Phe Gln Gln Lys Pro Gly Gln Pro Pro Lys Leu Leu Ile Tyr
1               5                   10                  15

<210> SEQ ID NO 49
<211> LENGTH: 32
<212> TYPE: PRT
<213> ORGANISM: Oryctolagus cuniculus

<400> SEQUENCE: 49

Gly Val Pro Ser Arg Phe Ser Gly Ser Gly Ser Gly Thr Gln Phe Thr
1               5                   10                  15

Leu Thr Val Ser Gly Val Gln Cys Asp Asp Ala Ala Thr Tyr Tyr Cys
            20                  25                  30

<210> SEQ ID NO 50
```

```
<211> LENGTH: 10
<212> TYPE: PRT
<213> ORGANISM: Oryctolagus cuniculus

<400> SEQUENCE: 50

Phe Gly Gly Gly Thr Glu Val Val Val Lys
1               5                   10

<210> SEQ ID NO 51
<211> LENGTH: 116
<212> TYPE: PRT
<213> ORGANISM: Oryctolagus cuniculus

<400> SEQUENCE: 51

Gln Ser Leu Glu Glu Ser Arg Gly Gly Leu Ile Lys Pro Gly Gly Thr
1               5                   10                  15

Leu Thr Leu Thr Cys Thr Val Ser Gly Phe Ser Leu Ser Tyr Ala
            20                  25                  30

Ile Ser Trp Val Arg Gln Ala Pro Gly Asn Gly Leu Glu Trp Ile Gly
        35                  40                  45

Phe Ile Val Gly Ser Ser Gly Ser Ala Tyr Tyr Ala Ser Trp Ala Lys
    50                  55                  60

Ser Arg Ser Thr Ile Thr Arg Asp Thr Asn Leu Asn Thr Val Thr Leu
65                  70                  75                  80

Lys Met Thr Ser Leu Thr Ala Ala Asp Thr Ala Thr Tyr Phe Cys Ala
                85                  90                  95

Lys Gly Leu Tyr Ser Gly Gly Asn Tyr Trp Gly Pro Gly Thr Leu Val
            100                 105                 110

Thr Val Ser Ser
        115

<210> SEQ ID NO 52
<211> LENGTH: 110
<212> TYPE: PRT
<213> ORGANISM: Oryctolagus cuniculus

<400> SEQUENCE: 52

Ala Val Leu Thr Gln Thr Pro Ser Pro Val Ser Ala Ala Val Gly Gly
1               5                   10                  15

Thr Val Ser Ile Ser Cys Gln Ser Ser Gln Ser Val Asp Glu Asn Asn
            20                  25                  30

Tyr Leu Ser Trp Phe Gln Gln Lys Pro Gly Gln Pro Pro Lys Leu Leu
        35                  40                  45

Ile Tyr Arg Ala Ser Thr Leu Glu Ser Gly Val Pro Ser Arg Phe Ser
    50                  55                  60

Gly Ser Gly Ser Gly Thr Gln Phe Thr Leu Thr Val Ser Gly Val Gln
65                  70                  75                  80

Cys Asp Asp Ala Ala Thr Tyr Tyr Cys Leu Gly Gly Tyr Ser Gly Tyr
                85                  90                  95

Ser Asp Asp Gly Phe Gly Gly Gly Thr Glu Val Val Val Lys
            100                 105                 110
```